United States Patent [19]

Borror et al.

[11] 4,178,447

[45] Dec. 11, 1979

[54] NOVEL SYNTHESIS OF 3,3-SUBSTITUTED DIHYDROBENZISOTHIAZOLE-1,1-DIOXIDES AND -2,3-DIHYDRONAPHTHO-1,2-THIAZINE-1,1-DIOXIDES

[75] Inventors: Alan L. Borror, Lexington; James W. Foley, Andover; Marcis M. Kampe, Brookline; John W. Lee, Jr., Harvard, all of Mass.

[73] Assignee: Polaroid Corporation, Cambridge, Mass.

[21] Appl. No.: 836,025

[22] Filed: Sep. 23, 1977

[51] Int. Cl.$^2$ .............................. C07D 275/06
[52] U.S. Cl. .................. 544/33; 260/239 R; 260/245.5; 544/62; 544/135; 544/368; 546/95; 546/198; 548/209
[58] Field of Search ............ 260/268 BC, 293.57, 260/304 A, 301, 293.57; 544/33, 135, 62; 546/95

[56] References Cited

FOREIGN PATENT DOCUMENTS 4020779  5/1974  Japan ............................ 260/304 A

OTHER PUBLICATIONS

Beilstein, "Hand Buch der Organischen Chemie", vol. 27, p. 534.
Houben-Weil, "Met. der Org. Chemie", vol. 13, (1970), pp. 189-190.
McClelland et al., "J. Chem. Soc.", (1940), pp. 323-327.
Abramovitch, R. A., et al., "J. Chem. Soc.", Perkin Translation I, 22, pp. 2589-2594 (1974).
"Protective Groups in Organic Chemistry," Editor J. F. W. McOmie, Plenum Press, N.Y., 1973 (Chap. IV, Haslam), pp. 145-147.
Dutt, S., J. Chem. Soc., 121, pp. 2389-2394 (1922).

*Primary Examiner*—Donald G. Daus
*Assistant Examiner*—Lisa Jones
*Attorney, Agent, or Firm*—Sybil A. Campbell

[57] ABSTRACT

This invention relates to a method of synthesizing certain 3-(carbocyclic aryl)-3-(4'-OP-carbocyclic aryl)-2,3-dihydrobenz[d]isothiazole-1,1-dioxides (and -2,3-dihydronaphtho[1,8-de]-1,2-thiazine-1,1-dioxides) by reacting (a) a 4-OP-carbocyclic aryllithium compound wherein P is a protecting group and (b) a 3-(carbocyclic aryl)benz[d]isothiazole-1,1-dioxide wherein said 3-(carbocyclic aryl) moiety is other than a 3-(4'-OP-carbocyclic aryl) moiety to give (c) the corresponding 3-carbocyclic aryl)-3-(4'-OP-carbocyclic aryl)-2,3-dihydrobenz[d]isothiazole-1,1-dioxide. The -2,3-dihydronaphtho[1,8-de]-1,2-thiazine-1,1-dioxides are prepared in the same manner by reacting a 3-(carbocyclic aryl)naphtho[1,8-de]-1,2-thiazine-1,1-dioxide with said 4'-OP-carbocyclic aryllithium compound.

In a further embodiment, the compounds synthesized according to the foregoing method are reacted with a carboxylic acid halide to give the corresponding 2-carbonyl-substituted 2,3-dihydrobenz[d]isothiazole-1,1-dioxide (or -2,3-dihydronaphtho[1,8-de]-1,2-thiazine-1,1-dioxides) followed by removing the protecting group, P, with weak acid to yield certain phenol and 1-naphthol sulfam(na)phthaleins useful, e.g., as optical filter agents and filter agent precursors in photography.

26 Claims, No Drawings

NOVEL SYNTHESIS OF 3,3-SUBSTITUTED DIHYDROBENZISOTHIAZOLE-1,1-DIOXIDES AND -2,3-DIHYDRONAPHTHO-1,2-THIAZINE-1,1-DIOXIDES

BACKGROUND OF THE INVENTION

1. Field of the Invention

This invention relates to a novel method of preparing certain phenol and 1-naphthol sulfamphthaleins and sulfamnaphthaleins useful as reagents in photography.

2. Description of the Prior Art

Various procedures have been reported for synthesizing 3-substituted-benz[d]isothiazole-1,1-dioxides and 3,3-disubstituted-2,3-dihydrobenz[d]isothiazole-1,1-dioxides from saccharin (3-oxo-2,3-dihydrobenz[d]isothiazole-1,1-dioxide) and from saccharin pseudo-chloride (3chlorobenz[d]isothiazole-1,1-dioxide). As reported by A. Mustafa et al, *J. Chem Soc.*, 1952, p. 1339, the treatment of saccharin pseudo-chloride with excess phenylmagnesium bromide gave the corresponding 3,3-diphenyl-2,3-dihydrobenz[d]isothiazole-1,1-dioxide in almost quantitative yield. Methyl-, ethyl-, n-propyl- and n-butylmagnesium halides were reported by these authors to react analogously. R. A. Abramovitch et al, *J. Chem. Soc., Perkin Trans I*, 1974(22), p. 2589, reviewed and reinvestigated the reactions of saccharins with alkyl and aryl Grignard reagents and found that either the 3-alkyl (or 3-aryl)-benz[d]isothiazole-1,1-dioxide and/or the open-chain tertiary alcohol, o-CR$_2$OH benzenesulfonamide wherein R is alkyl (or aryl) were obtained with one exception. When saccharin was treated with an excess of phenylmagnesium bromide in boiling tetrahydrofuran, 3,3-diphenyl-2,3-dihydrobenz[d]isothiazole-1,1-dioxide was obtained as the minor product together with the open-chain tertiary alcohol.

R. A. Abramovitch et al also investigated the reaction of saccharin and saccharin pseudo-chloride with organolithium compounds and found that the reaction of saccharin with alkyl- and aryllithium compounds, such as, n-butyllithium and p-methoxyphenyllithium in tetrahydrofuran at −78° C. gave the corresponding 3-substituted-benz[d]isothiazole-1,1-dioxide exclusively. In addition to this general method for synthesizing 3-alkyl (or 3-aryl)-benz[d]isothiazole-1,1-dioxides, the authors reported that the reaction of the pseudo-chloride with organolithium compounds, such as, n-butyllithium in tetrahydrofuran at −78° C. gave the corresponding 3,3-disubstituted-2,3-dihydrobenz[d]isothiazole-1,1-dioxide as the major product.

Besides the reactions with Grignard and organolithium reagents, Friedel-Crafts reactions with the saccharins also have been disclosed. Dutt, *J. Chem. Soc.*, 121, p. 2389 (1922) reported the condensation of saccharin with aromatic amines and phenols in the presence of concentrated sulfuric acid and also in the presence of fused zinc chloride. The resulting condensation products with saccharin were named "sulfamphthaleins" by analogy to "phthaleins" and "sulfonephthaleins." Though the structure of 3,3-di(4'-hydroxyphenyl)-2,3-dihydrobenz[d]isothiazole-1,1-dioxide (named "phenolsulfamphthalein") was assigned to the condensation product obtained with saccharin and phenol, it has been determined that the compound corresponding to the proposed structure has properties different from those reported, for example, colorless rather than pink in alkali and also, that the compound corresponding to the structure given could not be synthesized by repeating the procedures reported by Dutt.

Copending U.S. patent application Ser. No. 836,010 of Stanley M. Bloom, Alan L. Borror and James W. Foley filed concurrently herewith is directed to a method of synthesizing phenol and 1-naphthol sulfamphthaleins and sulfamnaphthaleins possessing a carbonyl group in the 2-position of the sulfam(na)phthalein ring. Depending upon the carbonyl group and the phenolic and/or naptholic substituents, the products of the synthesis may be employed as pH-sensitive indicator dyes, antihalo dyes or photographic optical filter agents. As disclosed and claimed therein, the method of preparing these compounds comprises reacting a 3-(4'-OP-carbocyclic aryl)-3-(carbocyclic aryl)-2,3-dihydrobenz[d]isothiazole-1,1-dioxide (or -2,3-dihydronaphtho[1,8-de]-1,2-thiazine-1,1-dioxide) wherein P is a protecting group compatible with organometallic reagents and a carboxylic acid halide in the presence of pyridine to yield the corresponding 2-carbonyl derivative. Optionally, the acylation may be carried out by sequentially reacting the said isothiazole compound with an alkali metal hydride to give the corresponding 2-alkali metal salt followed by reaction with the selected carboxylic acid halide. The acylated compound thus prepared is then treated with acid to remove the protecting group and yield the product.

The 3-(4'-OP-carbocyclic aryl)-3-(carbocyclic aryl)-2,3-dihydrobenz[d]isothiazole-1,1-dioxides and the corresponding -2,3-dihydronaphtho[1,8-de]-1,2-thiazine-1,1-dioxides employed as starting materials in the method of aforementioned application Serial No. (Case 5693) may be synthesized by reacting a 3-(4'-OP-carbocyclic aryl)benz[d]isothiazole-1,1-dioxide or a 3-(4'-OP-carbocyclic aryl)naphtho[1,8-de]-1,2-thiazine-1,1-dioxide and a carbocyclic aryllithium reagent as disclosed and claimed in copending U.S. patent application Ser. No. 836,008 of Alan L. Borror, Louis Cincotta, James W. Foley and Marcis M. Kampe filed concurrently herewith.

The present invention is concerned with a different method of synthesizing certain 3-(4'-OP-carbocyclic aryl)-3-(carbocyclic aryl)-2,3-dihydrobenz[d]isothiazole-1,1-dioxides (and -2,3-dihydronaphtho[1,8-de]-1,2-thiazine-1,1-dioxides) and with the use of these compounds in the preparation of certain of said phenol and 1-naphthol sulfamphthaleins and sulfamnaphthaleins possessing a carbonyl group in the 2-position of the sulfam(na)phthalein ring.

SUMMARY OF THE INVENTION

It is, therefore, the primary object of the present invention to provide a method of synthesizing compounds useful in the synthesis of certain phenol and 1-naphthol sulfam(na)phthaleins possessing a carbonyl group on the N atom of the sulfam(na)phthalein ring.

It is another object of the present invention to provide a method of preparing said N-substituted sulfam(na)phthaleins and of preparing intermediates therefor.

Other objects of this invention will in part be obvious and will in part appear hereinafter.

This invention accordingly comprises the process involving the several steps and the relation and order of one or more of such steps with respect to each of the others which are exemplified in the following detailed disclosure and the scope of the application of which will be indicated in the claims.

In one embodiment of the present invention, compounds useful in the preparation of the above-denoted N-substituted sulfamphthaleins are synthesized by reacting (a) a 4-OP-carbocyclic aryllithium compound wherein P is a protecting group and (b) a 3-(carbocyclic aryl)benz[d]isothiazole-1,1-dioxide wherein said 3-(carbocyclic aryl) moiety is other than a 3-(4'-OP-carbocyclic aryl) moiety to give (c) the corresponding 3-(carbocyclic aryl)-3-(4'-OP-carbocyclic aryl)-2,3-dihydrobenz[d]isothiazole-1,1-dioxide. The 2,3-dihydronaphtho[1,8-de]-1,2-thiazine-1,1-dioxides are prepared in the same manner except that a 3-(carbocyclic aryl)-naphtho[1,8-de]-1,2-thiazine-1,1-dioxide is reacted with the 4'-OP-carbocyclic aryllithium compound.

This method is applicable to the preparation of 3,3-disubstituted-2,3-dihydrobenz[d]isothiazole-1,1-dioxides and 3,3-disubstituted-2,3-dihydronaphtho[1,8-de]-1,2-thiazine-1,1-dioxides wherein one of the 3,3 substituents is a 4'-OP-phenyl moiety, unsubstituted or substituted with one or more substituents compatible with organometallic reagents, or a 4'-OP-naphthyl moiety, unsubstituted or substituted with one or more substituents compatible with organometallic reagents and the other of the 3,3 substituents is different and is other than a 4'-OP-phenyl and a 4'-OP-naphthyl moiety. These compounds are among those forming the subject matter of copending U.S. patent application Ser. No. 836,008 of Alan L. Borror, Louis Cincotta, James W. Foley and Marcis M. Kampe filed concurrently herewith.

For a fuller understanding of the nature and objects of the present invention, reference should be had to the following detailed description.

DESCRIPTION OF THE PREFERRED EMBODIMENTS

Specifically, the method of the present invention for preparing the above-denoted isothiazole and 1,2-thiazine-1,1-dioxide compounds comprises reacting (a) a 4-OP-carbocyclic aryllithium compound wherein P is a protecting group selected from 4-OP-phenyllithium, unsubstituted or substituted with one or more substituents compatible with organometallic reagents, the same or different, and 4-OP-naphthyllithium, unsubstituted or substituted with one or more substituents compatible with organometallic reagents, and (b) a compound of the formula

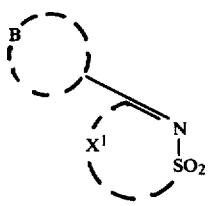

wherein B is a carbocyclic aryl moiety other than a 4'-OP-carbocyclic aryl moiety selected from a phenyl moiety, unsubstituted or substituted with one or more substituents compatible with organometallic reagents, the same or different, and a naphthyl moiety, unsubstituted or substituted with one or more substituents compatible with organometallic reagents, the same or different, and $X^1$ represents the atoms necessary to complete a benz[d]isothiazole-1,1-dioxide moiety or a naphtho[1,8-de]-1,2-thiazine-1,1-dioxide moiety in an inert solvent at a temperature between about −80° C. and 50° C. to give (c) the compound having the formula

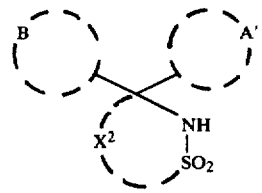

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; P is a protecting group; B has the same meaning given above; and $X^2$ represents the atoms necessary to complete a 2,3-dihydrobenz[d]isothiazole-1,1-dioxide moiety or a 2,3-dihydronaphtho[1,8-de]-1,2-thiazine-1,1-dioxide moiety.

The above reaction scheme is illustrated below using as specific reactants, 3,5-dimethyl-4-methoxyphenyllithium and 3-(4'-N-morpholinyl-1'-phenyl)benz[d]isothiazole-1,1-dioxide.

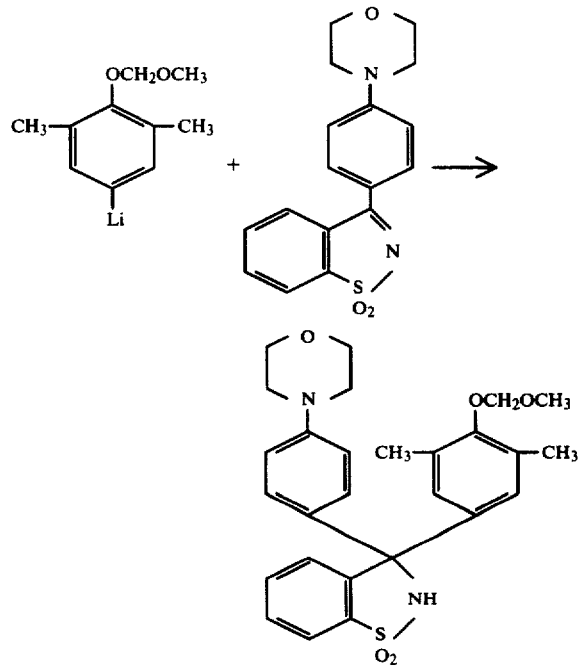

As indicated above, in the blocked compounds produced in accordance with the subject method, the 3,3 substituents are different. The A' moiety of these sulfam(na)phthaleins is derived from a blocked phenol or a blocked 1-naphthol and the B moiety is other than a blocked phenol or a blocked 1-naphthol.

The substituents selected for the A' and/or B moieties and, if desired, for the sulfam(na)phthalein moiety should be stable to organometallic reagents, such as, lithium and Grignard reagents and include substituents capable of being blocked during the synthesis by a protecting group that can be subsequently removed under weakly acid conditions simultaneously with the protecting group P used to block the functional —OH of the 4'-hydroxyphenyl or 4'-hydroxynaphthyl moiety.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

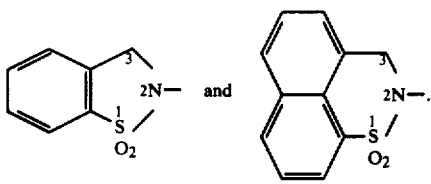

Typical of the sulfam(na)phthaleins that may be prepared according to the present invention are those represented by the following formula:

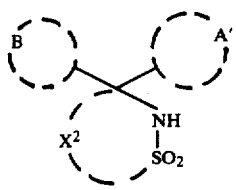

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety other than a 4'-OP-1'-phenyl moiety, unsubstituted or substituted with one or more substituents compatible with organometallic reagents, the same or different, or a naphthyl moiety other than a 4'-OP-1'-naphthyl moiety, unsubstituted or substituted with one or more substituents compatible with organometallic reagents, the same or different; P is a protecting group; and $X^2$ represents the atoms necessary to complete a 2,3-dihydrobenz[d]isothiazole-1,1-dioxide moiety or a 2,3-dihydronaphtho[1,8-de]-1,2-thiazine-1,1-dioxide moiety.

Typical substituents compatible with or capable of being protected to be compatible with organometallic reagents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenylhexyl and phenyldodecyl; alkoxy, such as, methoxy, ethoxy, butoxy, octadecyloxy, 1-ethoxy-2-($\beta$-ethoxyethyl); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—SO$_2$R$^0$ wherein R$^0$ is alkyl, aryl, alkaryl or aralkyl); sulfamoyl (—SO$_2$—NH—R$^0$ wherein R$^0$ has the same meaning given above); acyl

wherein R$^0$ has the meaning given above); sulfonyl (—SO$_2$—R$^0$ wherein R$^0$ has the same meaning given above); sulfo; cyano, carboxy, hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine).

As noted previously, the blocked sulfam(na)phthaleins synthesized in the manner described above may be employed in the preparation of certain phenol and 1-naphthol sulfam(na)phthaleins possessing a carbonyl group in the 2-position of the sulfam(na)phthalein ring and in the preparation of 2-substituted precursors therefor. In these embodiments, the subject method includes the additional step of reacting said compound (c) with an acid halide of the formula W-Z wherein W is chloro or bromo and Z is a carbonyl moiety containing a

group in pyridine at a temperature between about 0° C. and 100° C. to yield (d) the corresponding acylated compound having the formula

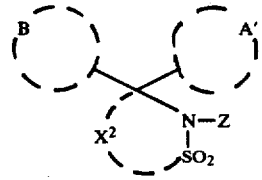

wherein A', B and $X^2$ have the same meaning given above and Z is said carbonyl moiety and said

is bonded to said N atom or reacting said compound (c) with MH wherein M is an alkali metal selected from lithium, sodium and potassium in an inert organic solvent at a temperature between about 0° C. and 100° C. to give the corresponding N-alkali metal salt followed by reacting said N-alkali metal salt with said acid halide, W-Z, to give said N-acylated compound (d), and to obtain the phenol and 1-naphthol sulfam(na)phthalein products includes the additional step of treating said compound (d) with an organic or inorganic acid at a pH between about 0.1 to 5.0 to give (e) the compound having the formula

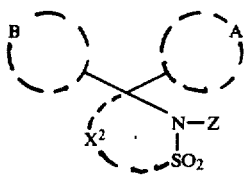

wherein A is a 4'-OH-1'-phenyl moiety, unsubstituted or substituted with one or more substituents compatible with organometallic reagents, the same or different, or a 4'-OH-1'-naphthyl moiety, unsubstituted or substituted with one or more substituents compatible with organometallic reagents, the same or different; and B, $X^2$ and Z have the same meaning given above.

In a preferred embodiment the method of the present invention comprises (1) reacting (a) a compound of the formula

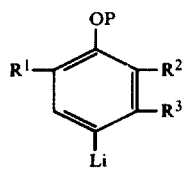

wherein P is a protecting group; $R^1$ and $R^2$ each are selected from hydrogen, alkyl, alkoxy, chloro and fluoro; $R^3$ is hydrogen, alkyl, alkoxy or —OP; and $R^2$ and $R^3$ taken together represent the carbon atoms necessary to complete a fused benzene ring and (b) a compound having the formula

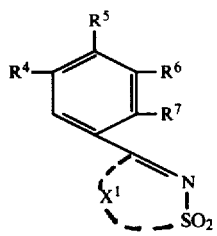

wherein $R^4$ and $R^6$ each are selected from hydrogen, alkyl, alkoxy, chloro and fluoro; $R^5$ is hydrogen, alkyl, alkoxy, —N,N-(dialkyl)amino, —N,N-(w-$R^8$alkyl)$_2$amino wherein $R^8$ is halo or —$OP^I$ wherein $P^I$ is a protecting group, —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —$OP^{II}$ wherein $P^{II}$ is a protecting group the same as $P^I$; $R^6$ and $R^7$ taken together represent the carbon atoms necessary to complete a fused benzene ring; $R^4$, $R^5$ and $R^6$ taken together represent the atoms necessary to complete a fused [ij]-quinolizidine ring and $X^1$ represents the atoms necessary to complete benz[d]isothiazole-1,1-dioxide or naphtho[1,8-de]-1,2-thiazine-1,1-dioxide in an inert organic solvent at a temperature between about −80° C. to 50° C. to give (c) the compound having the formula

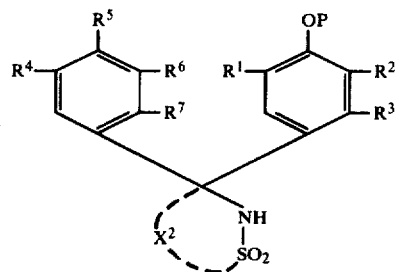

wherein P, $R^1$, $R^2$, $R^3$, $R^4$, $R^5$, $R^6$ and $R^7$ have the same meaning given above and $X^2$ represents the atoms necessary to complete 2,3-dihydrobenz[d]isothiazole-1,1-dioxide or 2,3-dihydronaphtho[1,8-de]-1,2-thiazine-1,1-dioxide, and in further embodiments includes the additional step(s) of (2a) reacting said compound (c) and an acid halide of the formula

wherein W is chloro or bromo and $R^9$ is methyl, methyl substituted with at least one halo group selected from chloro, bromo and fluoro, alkoxy having 1 to 4 carbon atoms, phenyl, phenyl substituted in the para position with alkyl having 1 to 4 carbon atoms or —N,N-(dialkyl)amino, phenyl substituted with at least one electron-withdrawing group, phenoxy, phenoxy substituted with at least one electron-withdrawing group, —O(CH$_2$)$_2$Y wherein Y is an electron-withdrawing group and phenyl substituted in the ortho position with —CH$_2$R$^{10}$ wherein R$^{10}$ is chloro or bromo in pyridine at a temperature between about 0° and 100° C. to yield (d) the corresponding N-acylated compound of the formula

wherein P, $R^1$, $R^2$, $R^3$, $R^4$, $R^5$, $R^6$, $R^7$, $R^9$ and $X^2$ have the same meaning given above; or (2b) sequentially reacting said compound (c) with MH wherein M is an alkali metal selected from lithium, sodium and potassium in an inert organic solvent at a temperature between about 0° C. and 100° C. to give the corresponding N-alkali metal salt having the formula

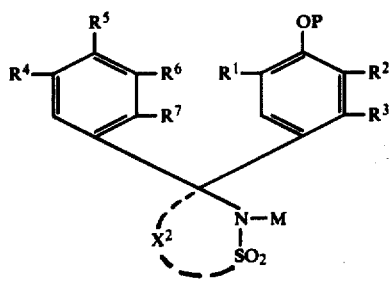

wherein P, $R^1$, $R^2$, $R^3$, $R^4$, $R^5$, $R^6$, $R^7$, $X^2$ and M have the same meaning given above and then reacting said N-alkali metal salt with said acid halide

to give said N-acylated compound (d); and (3) treating said compound (d) at a temperature between about 20° and 100° C. with an organic or inorganic acid at a pH between about 0.1 and 5.0 to yield the product having the formula

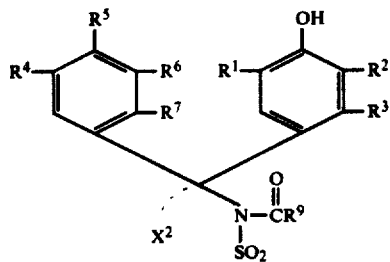

wherein $R^1$, $R^2$, $R^3$, $R^4$, $R^5$, $R^6$, $R^7$, $R^9$ and $X^2$ have the same meaning given above except that said —OP of $R^3$, said —$OP^I$ of $R^5$, and said —$OP^{II}$ of $R^7$ each are —OH.

Usually, the alkyl and alkoxy substituents comprising $R^1$, $R^2$, $R^3$, $R^4$, $R^5$, $R^6$ and $R^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N-(dialkyl)amino and —N,N-(w-$R^8$alkyl)$_2$-amino substituents usually are lower alkyl having 1 to 4 carbon atoms and $R^8$, when halo, is preferably chloro. Examples of electron-withdrawing groups include halo, e.g., fluoro, chloro and bromo; nitro; cyano; —$SO_2CH_3$;

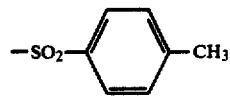

and —$COCH_3$. The sigma value for these and other groups have been reported by Eugene Müller, Methoden Der Organischen Chemie, Georg Thieme Verlag, Stuttgart, 1970, p. 78.

In a particularly preferred embodiment, $X^2$ represents the atoms necessary to complete 2,3-dihydrobenz[d]isothiazole-1,1-dioxide.

The above reaction sequence for producing N-substituted phenol and 1-naphthol sulfam(na)phthaleins and the N-substituted precursors therefor is illustrated below using as specific reactants, 3-(4'-N-morpholinyl-1'-phenyl)-3-(3'',5''-dimethyl-4''-methoxy-1''-phenyl)-2,3-dihydrobenz[d]isothiazole-1,1-dioxide and 2-cyanoethylchloroformate.

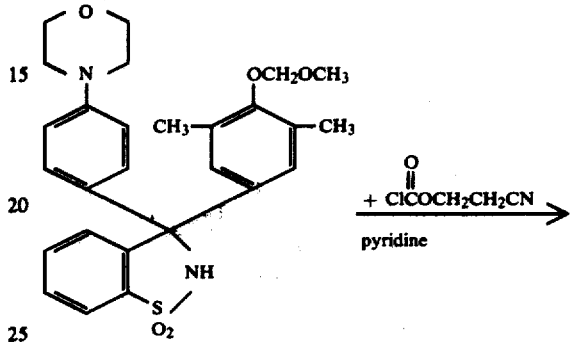

(2a)

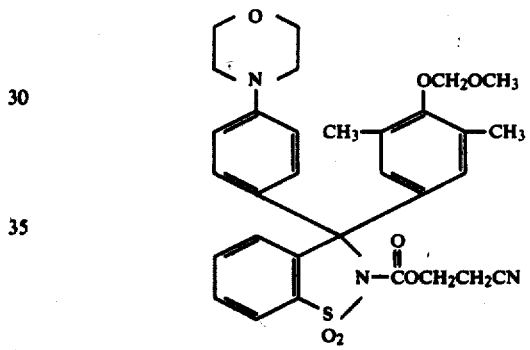

(2b)

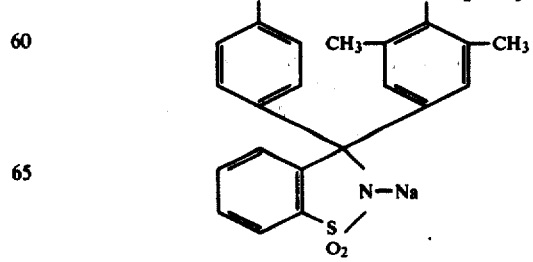

-continued
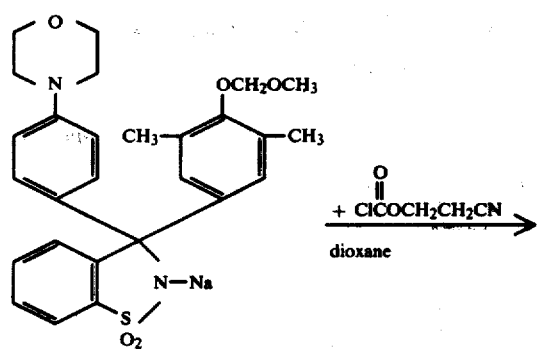
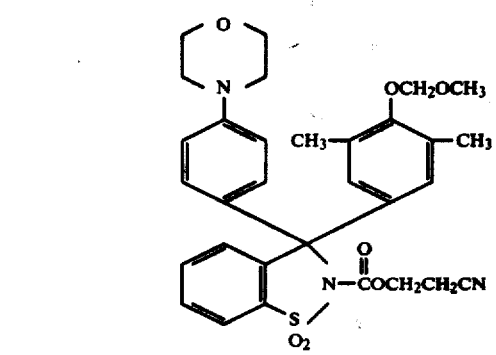
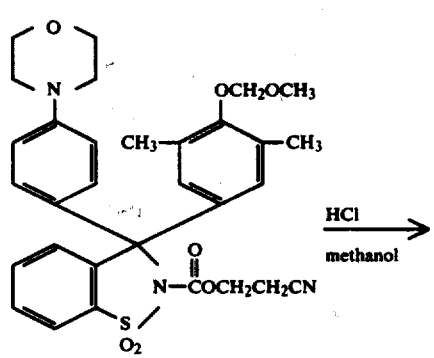
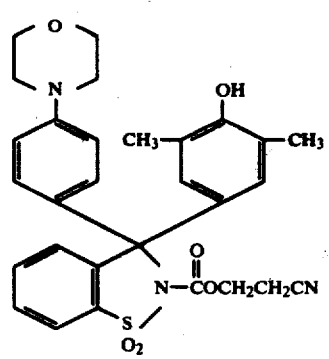
Specific examples of N-substituted phenol and 1-naphthol sulfam(na)phthaleins that may be prepared according to the present invention are as follows:
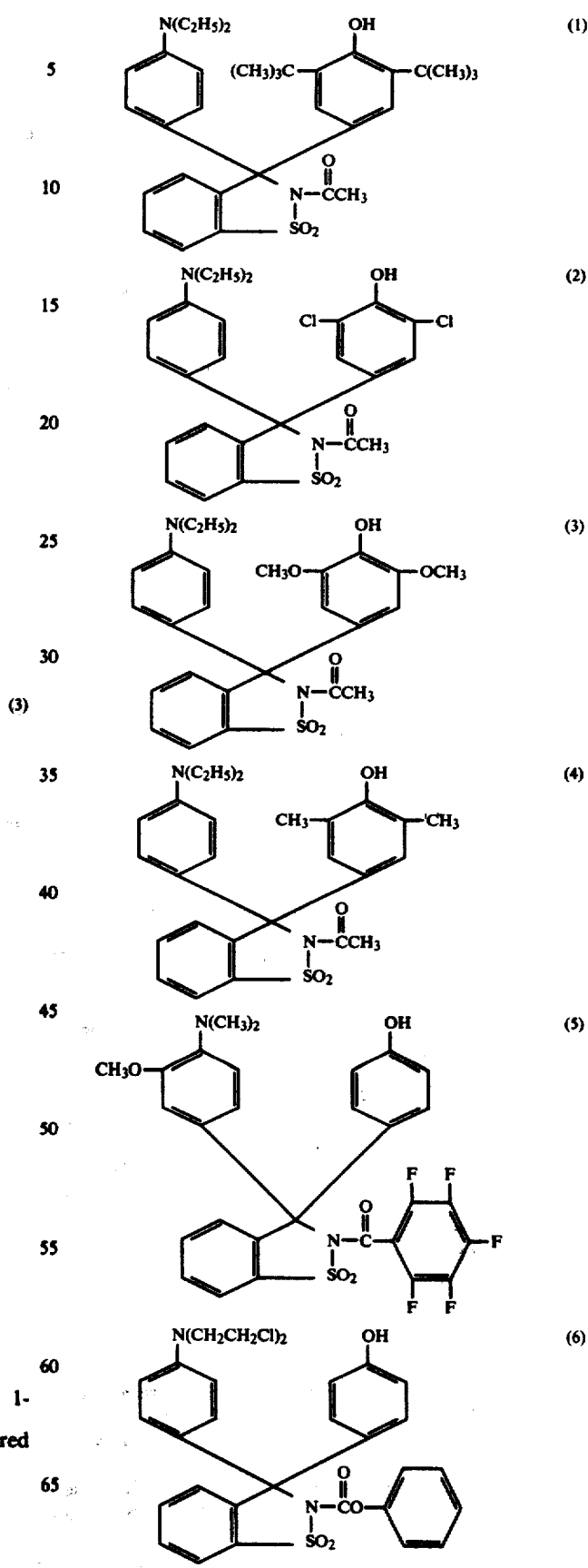

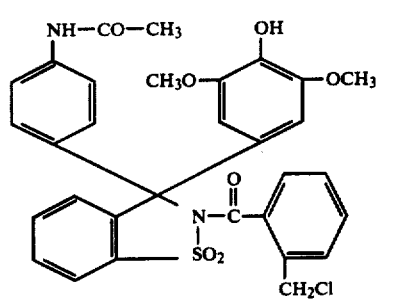 (7)
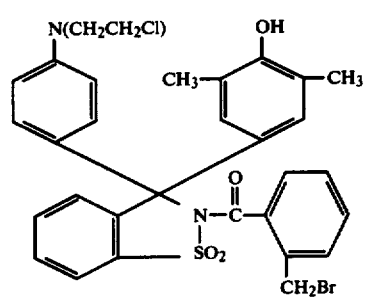 (8)
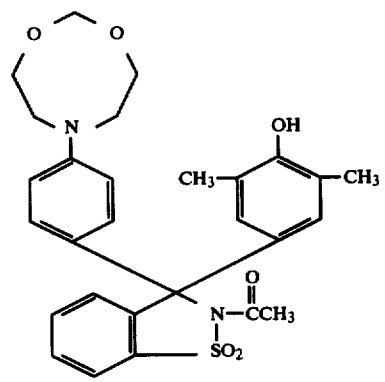 (9)
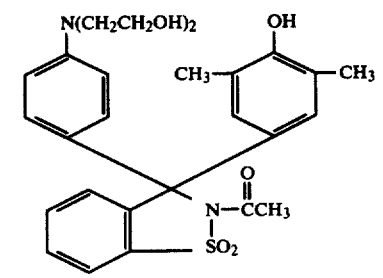 (10)
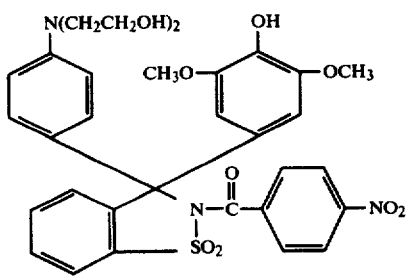 (11)
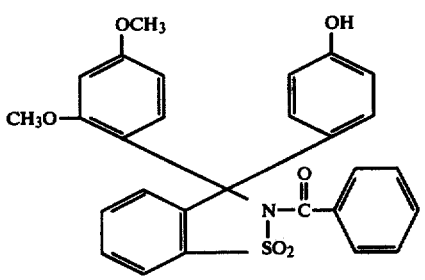 (12)
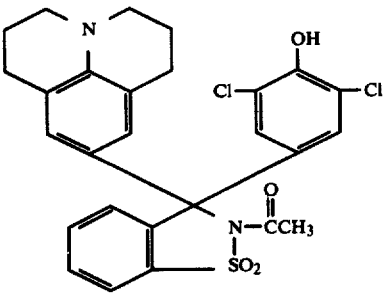 (13)
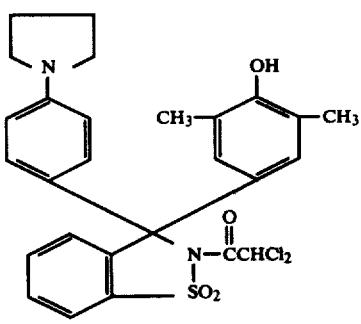 (14)
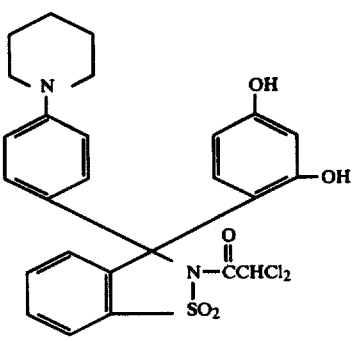 (15)
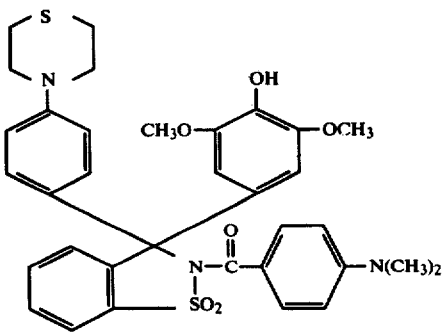 (16)

-continued
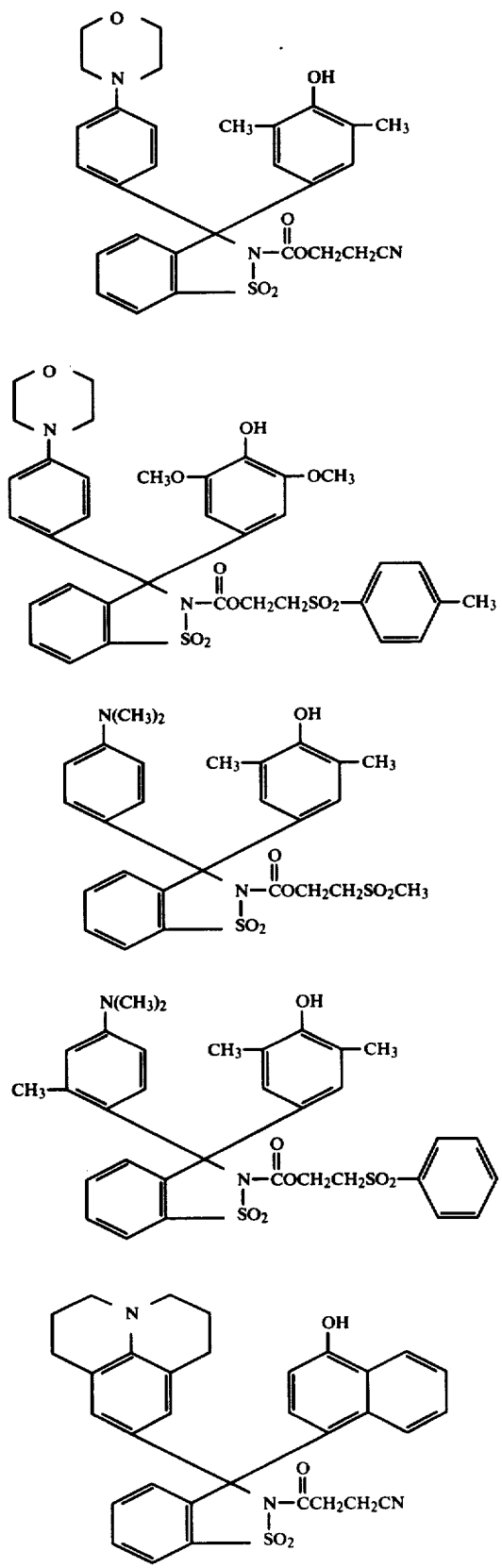
-continued
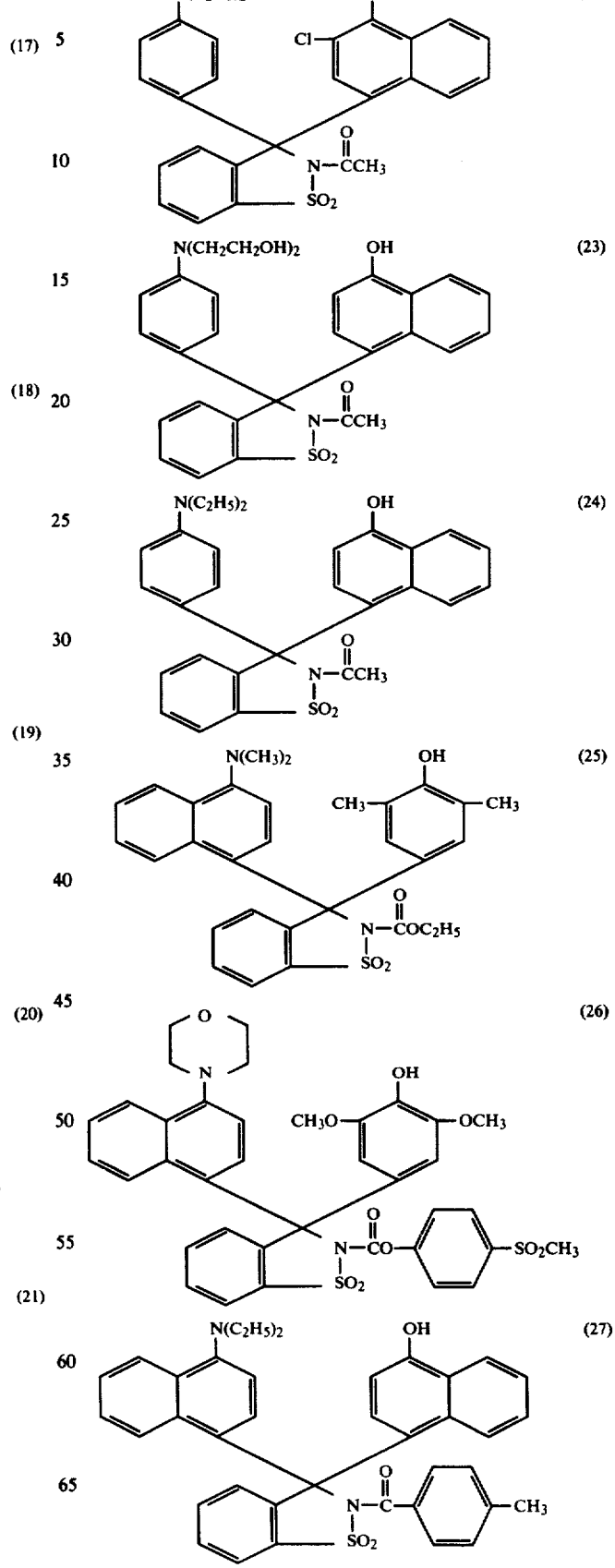

-continued

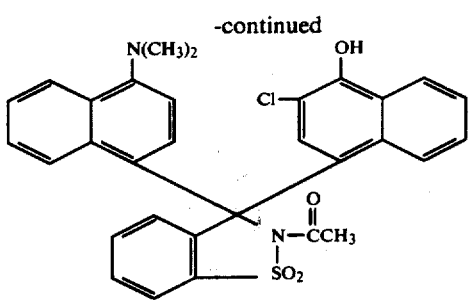 (28)

The respective intermediates obtained as the products of step (1) and of the N-acylation step (2a) or (2b) including the N-alkali metal salts produced in the first reaction of optional N-acylation step (2b) may be represented by the formula

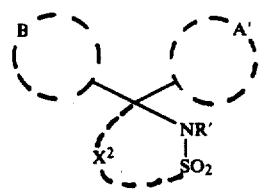

wherein A' is a 4'-OP-1'-phenyl moiety, unsubstituted or substituted with one or more substituents compatible with organometallic reagents, the same or different, or a 4'-OP-1'-naphthyl moiety, unsubstituted or substituted with one or more substituents compatible with organometallic reagents, the same or different; B is a phenyl moiety other than a 4'-OP-1'-phenyl moiety, unsubstituted or substituted with one or more substituents compatible with organometallic reagents, the same or different, or a naphthyl moiety other than a 4'-OP-1'-naphthyl moiety, unsubstituted or substituted with one or more substituents compatible with organometallic reagents, the same or different; P is a protecting group; $X^2$ represents the atoms necessary to complete a 2,3-dihydrobenz[d]isothiazole-1,1-dioxide moiety or a 2,3-dihydronaphtho[1,8-de]-1,2-thiazine-1,1-dioxide moiety; and R' is hydrogen, an alkali metal selected from sodium, potassium and lithium or a carbonyl moiety containing a

group bonded to said N atom.

Specific examples of such intermediates that may be prepared according to the present invention include

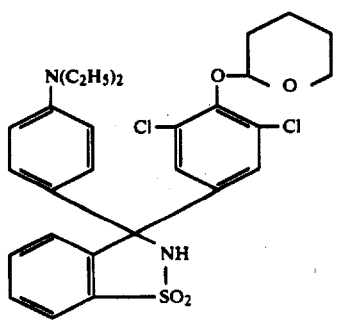 (29)

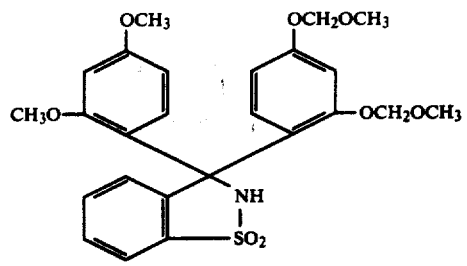 (30)

(31)

(32)

(33)

(34)

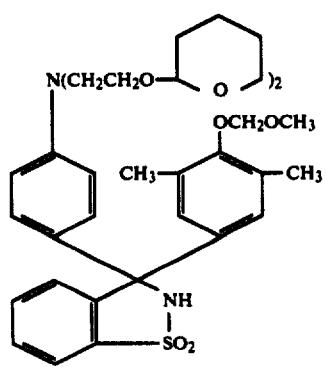
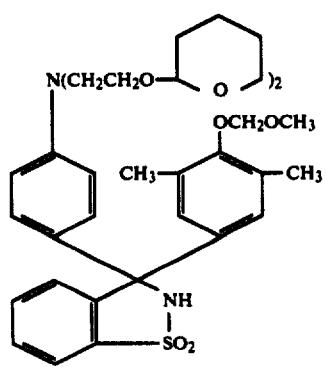

-continued
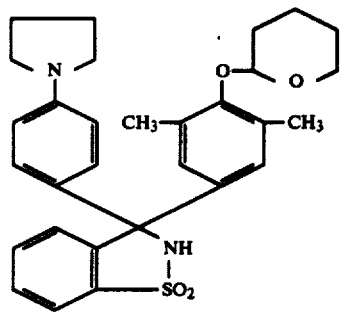 (35)
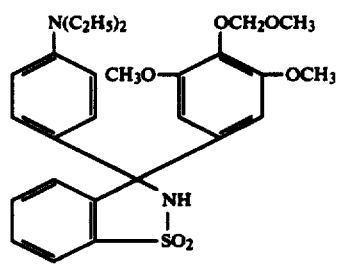 (36)
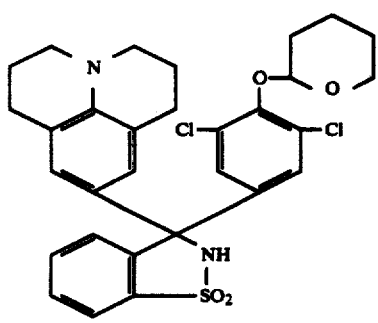 (37)
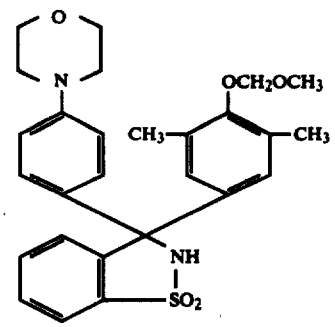 (38)
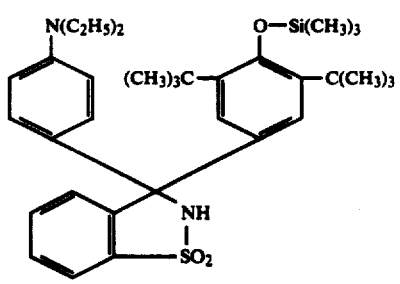 (39)
-continued
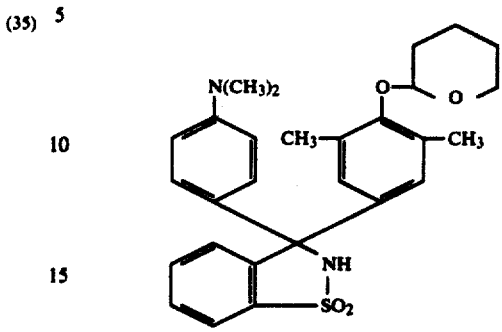 (40)
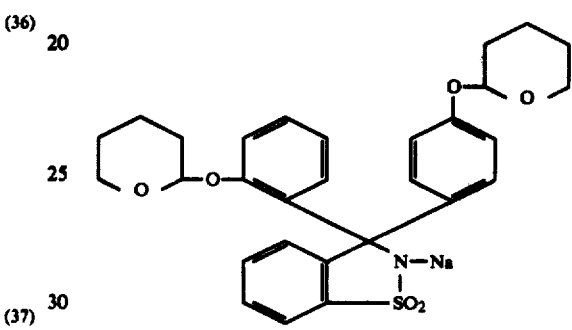 (41)
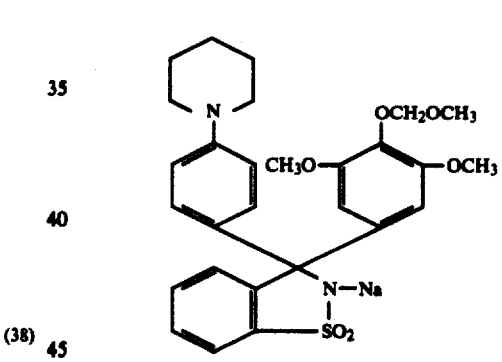 (42)
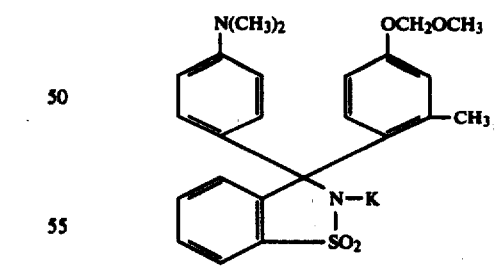 (43)
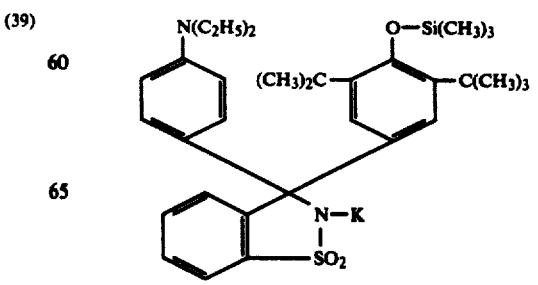 (44)

-continued
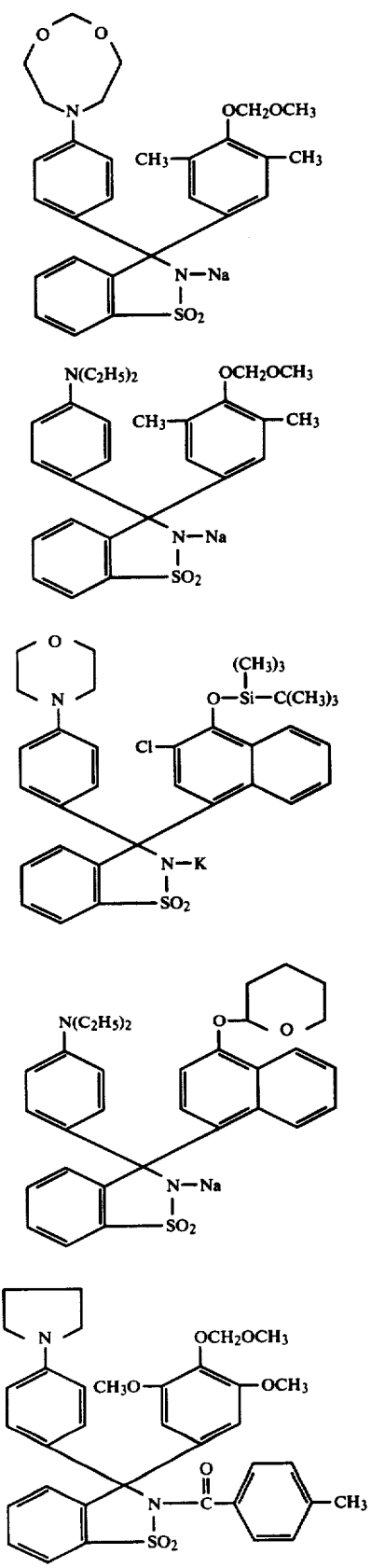
-continued
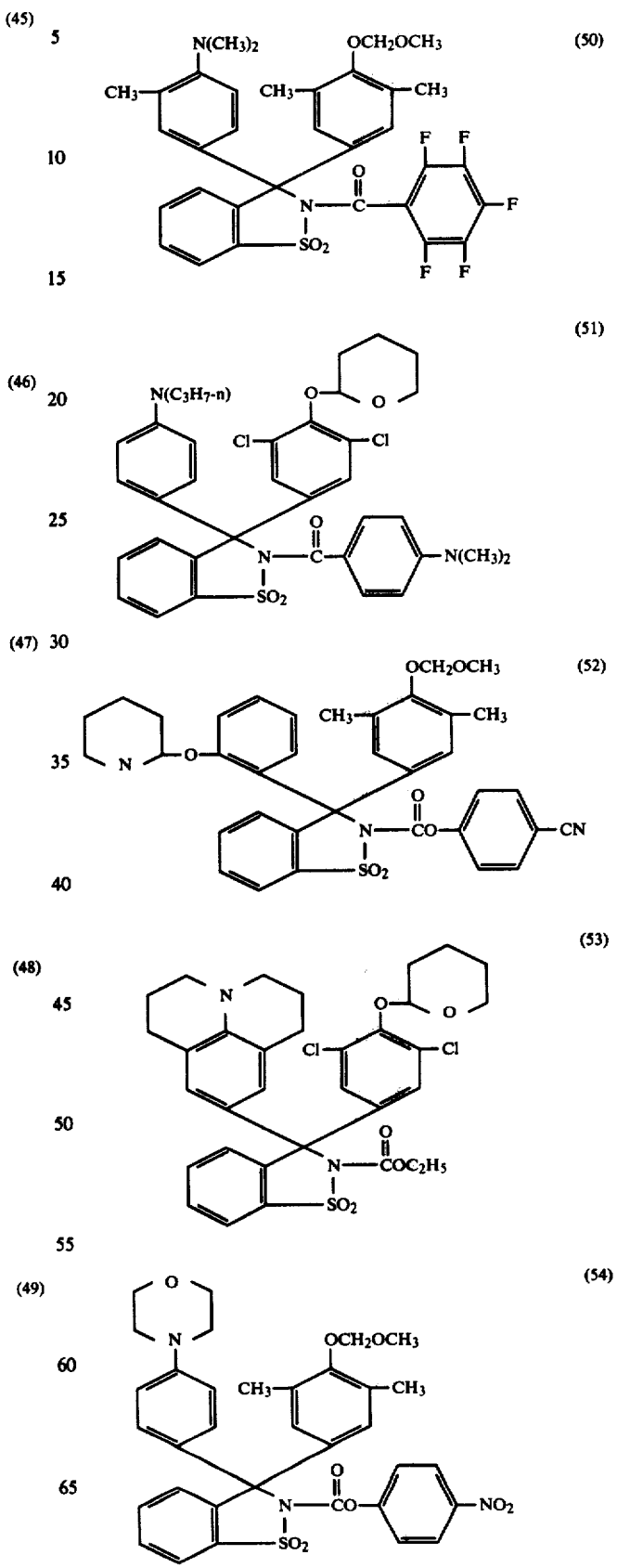

-continued
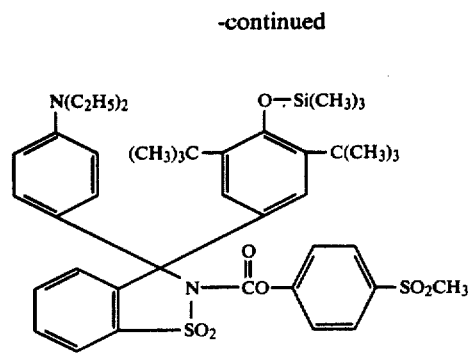 (55)
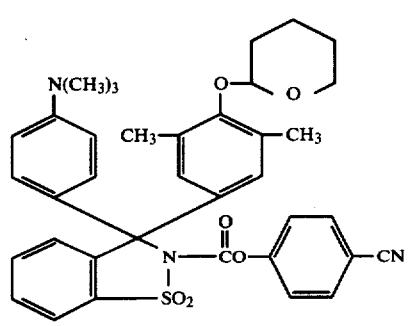 (56)
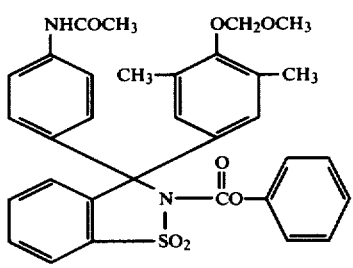 (57)
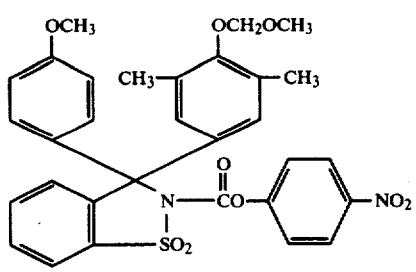 (58)
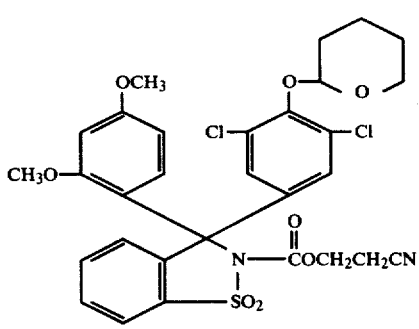 (59)
-continued
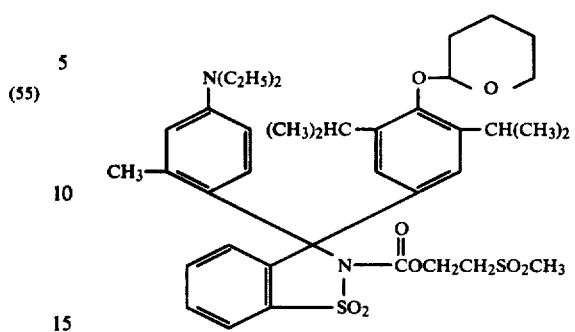 (60)
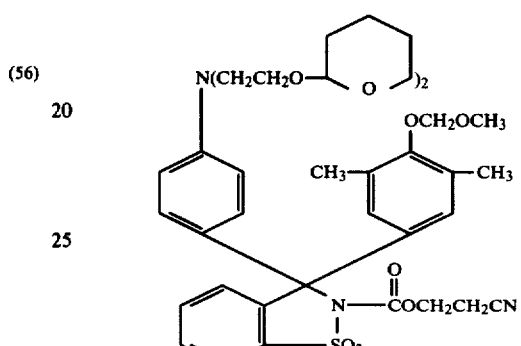 (61)
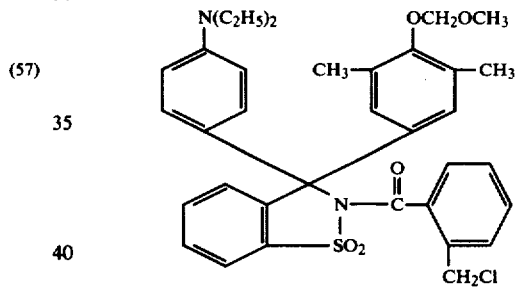 (62)
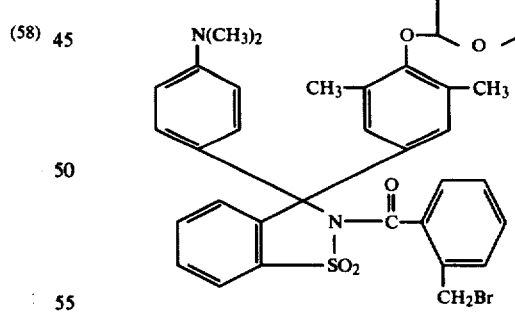 (63)
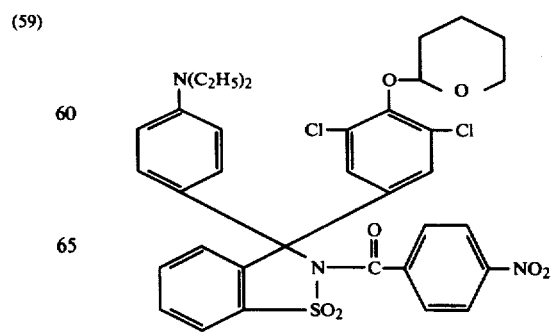 (64)

-continued

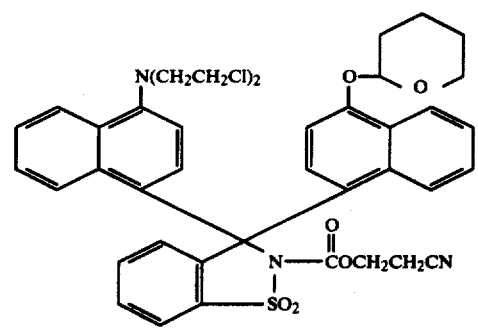 (65)

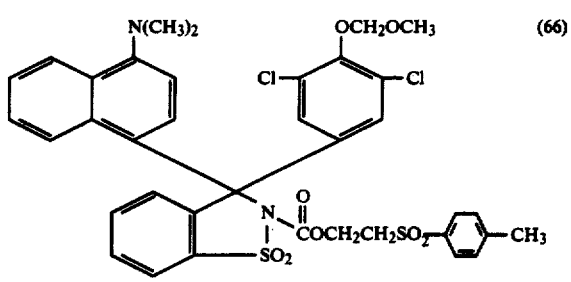 (66)

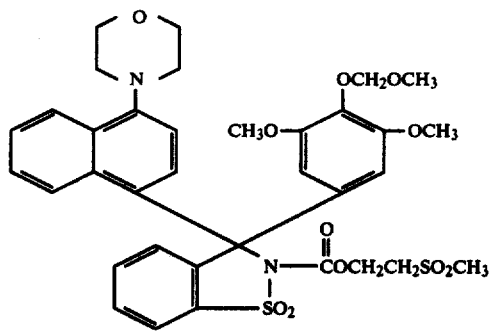 (67)

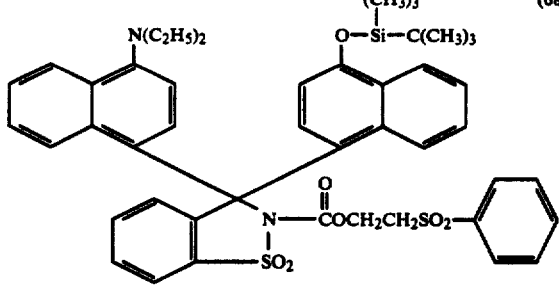 (68)

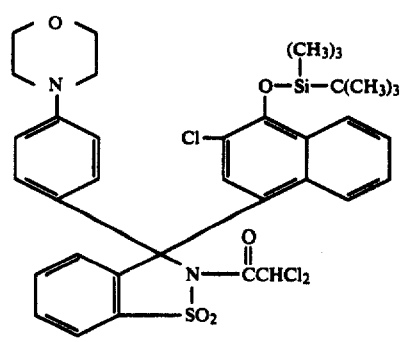 (69)

-continued

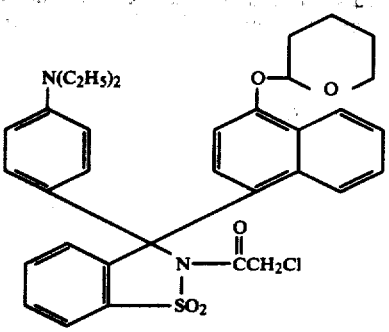 (70)

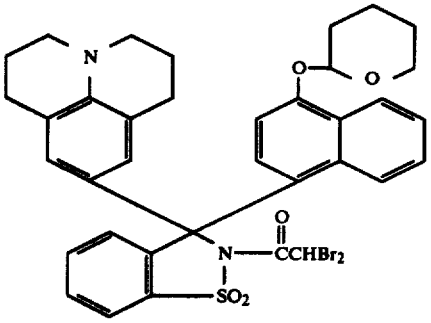 (71)

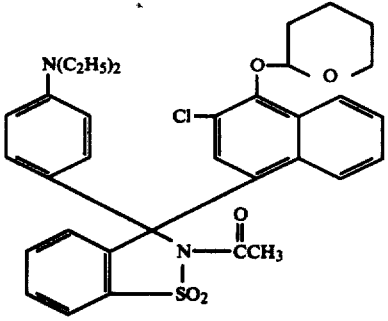 (72)

The 3-(phenyl/naphthyl)-benz[d]isothiazole-1,1-dioxides employed as starting materials in the subject method are prepared by blocking hydroxy and/or other substituent group(s), as may be appropriate, of the selected halo-benzene or halo-naphthalene compound and converting the halo compound to the corresponding Grignard or lithium reagent which is then reacted with a saccharin reagent. The halo substituent may be chloro, bromo or iodo when the lithium reagent is prepared by reaction with lithium metal and is either bromo or iodo when the lithium reagent is made via lithium exchange using, for example, n-butyllithium. In preparing the Grignard reagent by reaction with magnesium metal, the halo substituent may be chloro, bromo or iodo. The Grignard or lithium reagent thus prepared is then reacted with saccharin, the N-lithium salt of saccharin or saccharin pseudo-chloride to yield the corresponding 3-(phenyl/naphthyl)benz[d]isothiazole-1,1-dioxide. Generally, the Grignard reagent is reacted with the pseudo-chloride, and the lithium reagent is reacted with the N-lithium salt. The 3-(phenyl/naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof. 3-(Naphthyl)benz[d]isothiazole-1,1-dioxides wherein the naphthyl substituent is substituted with certain N-heterocyclic moieties form the subject matter of copending U.S. patent application Ser. No. 836,008 of Alan L. Borror, James W. Foley and John W. Lee, Jr. filed concurrently herewith.

The preparation of the 3-(phenyl/naphthyl)benz[d]isothiazole-1,1-dioxide starting materials is illustrated below.

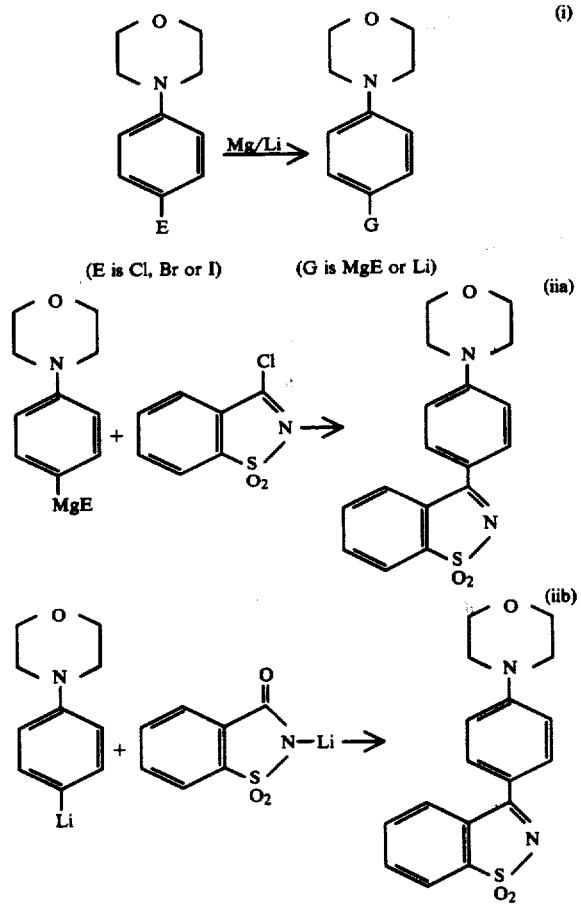

To prepare the 3-(phenyl/naphthyl)-3-(4'-OP-1'-phenyl/4'-OP-1'-naphthyl)-2,3-dihydrobenz[d]isothiazole-1,1-dioxides, the 3-(phenyl/naphthyl)benz[d]isothiazole-1,1-dioxide is reacted with an equimolar amount and usually with a slight excess of about 0.1 mole of a 4-OP-phenyllithium or a 4-OP-naphthyllithium reagent in an inert organic solvent, such as, benzene, diethyl ether, dioxane, hexane, toluene, petroleum ether or tetrahydrofuran. The reaction temperature may vary over a relatively wide range from about −80° to 50° C. as may be readily determined for the particular reagent. For achieving maximum yields, the reaction generally is conducted at a temperature below about 0° C.

The 4-OP-phenyl- or 4-OP-naphthyllithium reagent ultimately forming the A' moiety of the blocked intermediates and A of the ultimate sulfam(na)phthalein products may be substituted or unsubstituted and may be prepared from the corresponding halo-substituted compound. For example, a p-halophenol after blocking the functional —OH with an appropriate protecting group is reacted with lithium metal or n-butyllithium to yield the corresponding 4-OP-phenyllithium compound. When lithium metal is employed in the preparation of the lithium compound, the halo substituent may be chloro, bromo or iodo and is either bromo or iodo when a lithium exchange reaction is employed.

The p-halophenols and 4-halo-1-naphthols employed in the preparation of the lithium reagent, if not commercially available, may be prepared by methods known in the art by reacting the selected phenol or 1-naphthol with, for example, chlorine or bromine with or without a catalyst; N-bromosuccinimide or iodinemonochloride.

The groups selected for protecting the functional phenolic or naphtholic hydroxy group and other hydroxy groups that may be present in the phenol or 1-naphthol or any hydroxy group(s) present in the halobenzene or halonaphthalene compound should be stable to and compatible with organolithium and Grignard reagents and should protect the hydroxy group(s) against reaction under the conditions encountered in the preparation of the 4'-OP-carbocyclic aryllithium and 3-(carbocyclic aryl)benz[d]isothiazole-1,1-dioxide starting materials and in the subsequent steps in the synthesis of the N-acylated phenol and 1-naphthol sulfam(na)phthalein products. In addition, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the hydroxy group(s) of the phenol or 1-naphthol and of the halobenzene or halonaphthalene compound preferably is protected with methoxymethyl, 2'-tetrahydropyranyl or dimethyl-t-butylsilyl. The blocked compounds employing these protecting groups may be prepared by methoxymethylation as described, for example, by Kaoru Fuji et al, Synthesis, 4, pp. 276–277 (1975), by tetrahydropyranylation as described, for example, by William E. Parham et al, J. Amer. Chem. Soc., 70, pp. 4187–4189 (1948) or by silylating with dimethyl-t-butylsilyl chloride in the presence of imidazole as described by E. J. Corey et al, J. Amer. Chem. Soc., 94, pp. 6190–6191 (1972).

As indicated above, hydroxy groups in addition to the functional —OH of the phenol and 1-naphthol may be blocked simultaneously with the functional hydroxy group, for example, by tetrahydropyranylation or methoxymethylation. Substituents other than hydroxy that should be protected may be blocked prior to or subsequent to the blocking of the functional —OH. The protecting group selected should render such substituents compatible with organometallic reagents and should be removable under mildly acidic conditions so that the substituents can be regenerated simultaneously with the regeneration of the functional —OH of the phenolic or naphtholic moiety, i.e., the A moiety of the product sulfam(na)phthalein. As an example, carboxy group(s) may be protected by reacting a carboxy-substituted 4-halophenol (or 4-halo-1-naphthol) with 2-amino-2-methyl-1-propanol followed by blocking of the functional —OH. Sulfonamido (—NH—SO$_2$—R*) and sulfamoyl (—SO$_2$—NH—R*) substituents may be protected by a t-butyl group. It will be appreciated that hydroxy and/or other substituent(s) present in the halobenzene or halonaphthalene that should be protected are blocked in the same manner prior to conversion to the corresponding lithium compound for reaction with the saccharin reagent.

To prepare the N-acylated precursors for the phenol and 1-naphthol sulfam(na)phthalein products, the 3-(phenyl/naphthol)-3-(4'-OP-phenyl/4'-OP-naphthyl)-2,3-dihydrobenz[d]isothiazole-1,1-dioxides prepared as described above are reacted with a carboxylic acid halide in pyridine solution to give the corresponding N-acylated compound. About 1 to 2 moles of acid halide are used for each mole of the isothiazole-1,1-dioxide. Since the reaction is exothermic, external heating may not be necessary, but the reaction mixture may be heated to facilitate completion of the reaction, if desired. Ordinarily, the reaction temperature ranges between about 0° and 100° C., and preferably, the reaction is conducted in an inert atmosphere, for example, under nitrogen.

Optionally, the acylation step may be carried out by first reacting the isothiazole-1,1-dioxide with an equimolar amount or slight excess (~0.1 M) of an alkali metal hydride, MH, wherein M is sodium, potassium or lithium in an inert organic solvent at about 0° to 100° C., preferably in an inert atmosphere, and then reacting the N-alkali metal salt thus formed with the carboxylic acid halide. Usually the acid halide is added to the reaction mixture containing the N-alkali metal salt. However, the N-alkali metal salt may be isolated prior to reaction with the acid halide, if desired. Solvents suitable for use in the alternate method of forming the N-acylated compound include dioxane, tetrahydrofuran, ethyl ether and benzene. The alkali metal, like the pyridine, affords substitution of the ring nitrogen of the isothiazole moiety in the acylation reaction.

Carboxylic acid halides are well known and may be prepared in a conventional manner, for example, by reacting the selected carboxylic acid, RCOOH, with phosphorus trichloride, phosphorus pentachloride or thionyl chloride to give the corresponding RCOCl, or by reacting the selected ROH with phosgene to give the corresponding ClCOOR.

Subsequent to the acylation step, the protecting group P is removed from the functional —OH by treating with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above. As indicated previously, any other protecting groups that may be present are removed simultaneously with the protecting group on the functional —OH.

The following examples are given to further illustrate the present invention and are not intended to limit the scope thereof.

EXAMPLE 1

Preparation of the compound having the formula:

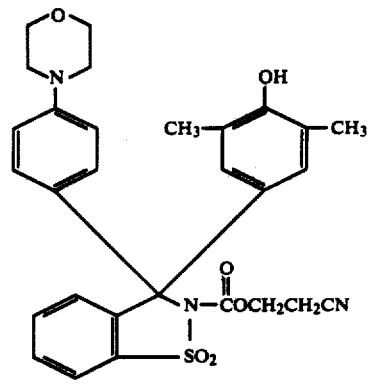

(a) 4-Bromo-2,6-dimethyl-methylenemethoxyphenyl ether (1.4 g.; 0.006 mol.) was dissolved in 30 ml. of dry tetrahydrofuran under nitrogen and cooled to −65° C. 2.5 ml. of n-butyllithium (2.4 M in hexane) was slowly added and the mixture was stirred at −65° C. for one hour. 3-(4'-N-morpholinyl-1'-phenyl)benz[d]isothiazole-1,1-dioxide (2.0 g.; 0.006 mol.) was added to the mixture which was stirred for one hour at −65° C. and for one hour at 50° C. The reaction mixture was then poured into water, the pH adjusted to 6 with conc. HCl and the mixture extracted with methylenechloride. The methylenechloride was dried and evaporated to give 2.8 g. of a yellow solid which was dissolved in 80 ml. of an ethyl ether:aqueous 1 N NaOH solution. After stirring for one-half hour, the basic aqueous layer was separated, washed with ether and neutralized with HCl to give 1.4 g. of a pale yellow solid. The solid was dried and recrystallized from methanol to give 3-(4'-N-morpholinyl-1'-phenyl)-3-(3'',5''-dimethyl-4''-methoxymethoxy-1''-phenyl)-2,3-dihydrobenz[d]isothiazole-1,1-dioxide (0.77 g.) having the formula

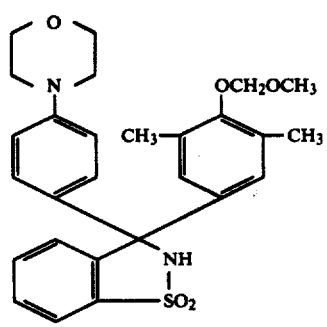

(b) The compound prepared in step (a) (0.7 g.) was placed in 20 ml. of pyridine under nitrogen and 0.15 ml. of β-cyanoethylchloroformate (ClCO₂CH₂CH₂CN) was added to the pyridine solution. The resulting reaction solution was stirred 1 hour, warmed gently and then poured into 100 ml. of water and extracted with chloroform. The chloroform was dried over Na₂SO₄, evaporated and the solid that formed was extracted with ligroin (boiling range 30°–60° C.). The solid obtained was the N-acylated compound, 3-(4'-N-morpholinyl-1'-phenyl)-3-(3'',5''-dimethyl-4''-methoxymethoxy-1''-phenyl)-2-(β-cyanocarbethoxy)-2,3-dihydrobenz[d]isothiazole-1,1-dioxide having the formula

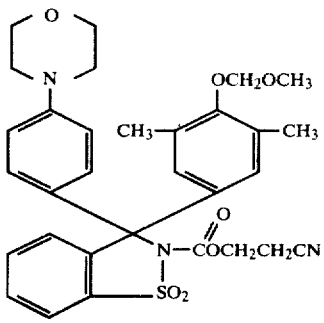

(c) The compound obtained in step (b) was then dissolved in methanol, made acidic with conc. hydrochloric acid and refluxed 1 hour. TLC from ether on silica gel showed 4 spots. The methanol solution was evaporated to leave 0.6 g. of solid. 200 mg. of solid in ether was placed on silica gel 1000 plates and the dark band was removed after drying plates. Acetone was used to remove the N-acylated product from the silica gel. The acetone was removed, ether added and the solution refluxed. The white solid that formed was recovered by filtration to give the title compound.

The 3-(4'-N-morpholinyl-1'-phenyl)benz[d]isothiazole-1,1-dioxide used in step (a) above was prepared as follows:

(i) 25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of N-(p-bromophenyl)morpholine as white crystals.

(ii) N-(p-bromophenyl)morpholine (30 g., 0.124 mol.) prepared as in step (i) was dissolved in 200 ml. of dry tetrahydrofuran under nitrogen and cooled to −60° C. to −70° C. To the resulting white slurry was added 2.4 M n-butyllithium (51.6 ml., 0.124 mol.) While keeping the temperature below −60° C. After the addition was complete, the reaction mixture was stirred for 1 hour at −70° C. to −60° C.

(iii) A tetrahydrofuran solution of the N-lithium salt of saccharin (0.124 mol.) was slowly added to the reaction mixture of step (ii) through a double ended needle and the mixture was stirred for 1 hour at −70° C. to −60° C. The resulting pale gray slurry was allowed to come slowly to room temperature turning into a dark solution, then orange. The reaction mixture was poured into 150 ml. of water, the pH adjusted to about 6 and extracted with ethyl ether. The ether was partially evaporated and allowed to stand. 11.0 grams of yellow crystals were collected. The mother liquor was evaporated to give 9.8 g. of green solid which was dissolved in hot benzene containing a trace of toluenesulfonic acid. The solution was refluxed with a Dean-Stark trap for 2 hours. The benzene was evaporated and the solid washed with acetone to yield 8.94 g. of yellow solid which was combined with the previously collected yellow crystals to give a total weight of 19.9 g. of the title compound.

The N-lithium salt of saccharin was prepared as follows:

Saccharin (22.7 g., 0.124 mol.) was dissolved in about 300 ml. of dry tetrahydrofuran under nitrogen and cooled to −65° C. n-Butyllithium (2.4 M) was added dropwise until a persistent peach color occurred. The solution was stirred at −60° C. to −65° C. for 1 hour and then used directly in step (iii) above.

The 4-bromo-2,6-dimethyl-methylenemethoxy phenyl ether used in step (a) above was prepared as follows:

Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30–45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenyl ether as a colorless oil (boiling point 112° C. and 0.5 mm Hg).

The β-cyanoethylchloroformate having the formula (CNCH$_2$CH$_2$COOCl) used in step (b) above was prepared as follows:

To 100 ml. of dry benzene, cooled in an ice bath, was added phosgene gas until 34.0 g. was collected. Hydroxyacrylonitrile (20.2 g.) was added to the cooled phosgene solution. (The temperature rose slightly to approximately 8° C.). The resulting heterogeneous mixture was cooled to 3° C. with stirring, and pyridine (22.6 g.) in 25 mls. of benzene was added dropwise. Heat was evolved, and the temperature was not allowed to rise above 10° C. Very vigorous stirring was maintained until solid began to form. After about 1 hour, the reaction mixture was stirred at approximately 5° C. for 15 minutes, then allowed to come to 15° C.–20° C. and stirred for another 15 minutes. The reaction mixture was then cooled to 5° C. and 26 ml. of ice water was added in increments. The solids dissolved with liberation of heat and evolution of gas. The temperature was not allowed to rise above 15° C. over the next 15–20 minutes. The reaction mixture was then stirred at room temperature for 2 hours, the benzene layer decanted and dried over anhydrous Na$_2$SO$_4$, followed by drying over anhydrous CaSO$_4$. The solvent was removed under reduced pressure to yield an almost colorless oil which was redistilled under vacuum at a boiling range of 68.5°–70.5° C. (pot temperature 98°–103° C.) to yield 18.2 g. of the title compound as a colorless oil.

EXAMPLE 2

Preparation of the compound having the formula

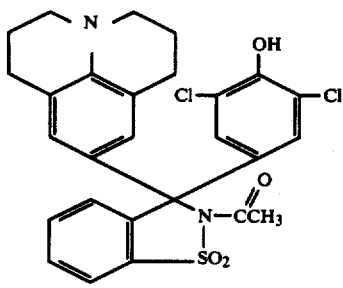

(a) 2'-Tetrahydropyranyl 4-bromo-2,6-dichlorophenyl ether (1.0 g.) was dissolved in 50 ml. of dry tetrahydrofuran under nitrogen at −65° C. The solution was stirred for ¾ hours with 1.29 ml. of 2.4 M butyllithium and then 3-(9'-julolidinyl)benz[d]isothiazole-1,1-dioxide (1.0 g.) was added. The resulting reaction mixture was allowed to warm to 0°–5° C. over one hour, stirred for one hour, cooled to −30° C. and poured into 150 ml. of water. The pH was adjusted to 6 with conc. HCl, and the mixture was extracted with 300 ml. of ether. The ether extracts were dried and evaporated to give 1.34 g. of an orange solid. The solid was run through a silica gel column with a solution of 8:2 ether/petroleum ether, and 1.0 g. of 3-(9'-julolidinyl)-3-[3'',5''-dichloro-4''-(2''-tetrahydropyranyloxy)-1''-phenyl]-2,3-dihydrobenz[d]isothiazole-1,1-dioxide was collected.

(b) The compound obtained in step (a) (1.0 g.) was dissolved in 50 ml. of pyridine and 0.3 ml. of acetyl chloride was added. The reaction mixture was stirred at room temperature for 2¼ hours, poured into 150 ml. of water and extracted with ether. The ether extract was dried and the solvent evaporated leaving an orange solid. The solid was run through a silica gel column with a solution of 8:2 ether/petroleum ether, and 0.47 g. of the 2-acetyl derivative of the compound prepared in step (a) was collected.

(c) The 2-acetyl compound prepared in step (b) was dissolved in 30 mls. of methanol. 3 drops of conc. HCl were added and the solution was refluxed for 15 minutes on a steam bath. The solution was cooled and the pH adjusted to 6. Preparative TLC gave 0.4 g. of the title compound.

3-(9'-julolidinyl)benz[d]isothiazole-1,1-dioxide was prepared as follows:

(i) Julolidine (100.4 g., 0.579 mol.) was dissolved in 266 ml. of glacial acetic acid. At room temperature, a solution of 29.69 ml. of bromine (0.579 mol.) in 1830 ml. of glacial acetic acid was slowly added to the julolidine solution over a period of about 2¼ hours. After the addition was complete, the reaction mixture was stirred for 1 hour. A potassium iodide test for excess bromine indicated no excess present. An additional 1 ml. of bromine was added to the reaction mixture, and the mixture was stirred for ½ hour. The potassium iodide test was repeated and indicated that excess bromine was present. 1000 ml. of ether was added to the reaction mixture which was neutralized by adding 127 ml. (0.637 mol.) of 5 N sodium hydroxide. The reaction mixture was further diluted with water and extracted with 2.7 liters of ether. The ether extracts were dried and evaporated to yield a dark oil (105.6 g.). The oil was redissolved in ether and washed with H₂O, the ether was dried over Na₂SO₄ and evaporated to yield a dark oil. The oil was distilled under reduced pressure with a short column to yield three fractions. First fraction, boiling range 123°–125° C. at 11 mm (starting material). Second fraction, boiling range 114°–115° C. at 0.06 mm (mixture). Third fraction, boiling range 120°–122° C. at 0.04 mm (pot temperature 160°–180° C.) contained 21.64 g. of 9-bromo-julolidine.

(ii) Saccharin (0.08 mol.) was dissolved in about 200 ml. of dry tetrahydrofuran under nitrogen and cooled to −65° C. n-Butyllithium (2.4 M) was added dropwise until a persistant peach color occurred. The solution was stirred at −60° C. to −65° C. for 1 hour.

(iii) The bromojulolidine prepared in step (i) (20.93 g., 0.08 mol.) was dissolved in 200 ml. of dry tetrahydrofuran under nitrogen and cooled to −60° C. to −70° C. n-Butyllithium was added slowly over one-half hour while maintaining the temperature below −60° C. After the addition was complete, the mixture was stirred for 1¼ hours at −60° C. With a double-ended needle, the slurry prepared in step (ii) was added to the mixture over 1 hour and stirred for 1 hour at −60° C. The reaction mixture was allowed to come to room temperature in the dark, stirred for 15 hours at room temperature and then hydrolyzed with 100 ml. of saturated ammonium chloride. The mixture was extracted with ether, and the ether extract was evaporated to give 15.40 g. of an orange solid. The solid was dissolved in about 400 ml. of methanol with about 20 drops of conc. HCl and refluxed for 4¼ hours. (The orange solid showed a small peak at 466 nm and a larger one at 380 nm and after refluxing one large peak occurred at 466 nm and none at 380 nm.) The acidic methanol was cooled and filtered, and 6.55 g. of product was collected as a dark red solid. The remaining mother liquor (methanol) was evaporated to yield 9.04 g. of a dark oil. The oil was run through a silica column with chloroform and an additional 1.34 g. of product was collected to yield a total of 7.89 g. of the title compound.

EXAMPLE 3

Preparation of the compound having the formula

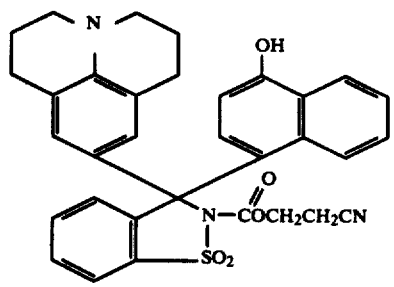

The title compound was prepared according to the procedure given in Example 2 except that the 2'-tetrahydropyranyl ether of 4-bromo-1-naphthol was used in step (a) and β-cyanoethylchloroformate was used as the acylating agent in step (b).

The 2'-tetrahydropyranyl ether of 4-bromo-1-naphthol was prepared as follows:

4-Bromo-1-naphthol (12.16 g.) was mixed with 250 ml. of dichloromethane at room temperature. To the resulting slurry was added 125 ml. of dihydropyran and then 13 drops of conc. HCl were added. The clear, straw-colored reaction solution was stirred at room temperature for approximately 3 hours, transferred to a separatory funnel, washed with about 400 ml. of aqueous 10% sodium hydroxide and the dichloromethane layer dried over anhydrous sodium sulfate. After drying, the dichloromethane solution was filtered through fresh anhydrous sodium sulfate, and the pale straw filtrate was evaporated under reduced pressure leaving 25.9 g. of straw yellow oil. The oil was applied directly to a wet packed SiO2 column (100-200 mesh: 4/1 petroleum ether/ether) and eluted with 4/1 petroleum ether/ether. Twenty-four fraction of about 50 ml. each were collected, and fractions 9-24 were combined and evaporated to give 16.91 g. of straw syrup which upon standing crystallized to give the title compound as pale lemon crystals.

EXAMPLE 4

Preparation of the compound having the formula

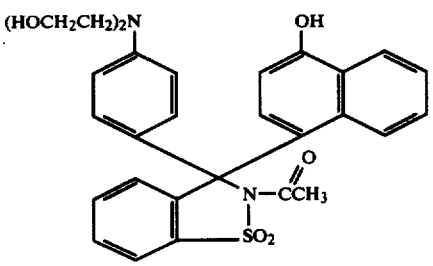

(a) The 2'-tetrahydropyranyl ether of 4-bromo-1-naphthol (1.5 g.) was dissolved in 30 ml. of anhydrous tetrahydrofuran under nitrogen and cooled to −65° C. To this solution was added 2 ml. of n-butyllithium (2.4 M in hexane). The solution was stirred for 30 minutes at −65° C. and 3-[4'-N,N-di-($\beta$-2''-tetrahydropyranyloxyethyl)-1'-phenyl]benz[d]isothiazole-1,1-dioxide (2.5 g.) was then added all at once. The resulting reaction mixture was stirred for two hours, poured into water and extracted with ether. The ether extract was filtered and the solvent evaporated to near dryness. Preparative TLC gave 0.03 g. of 3-[4'-N,N-di($\beta$-2''-tetrahydropyranyloxyethyl)-1'-phenyl]-3-[4'''-(2'''-tetrahydropyranyloxy)-1''-phenyl]-2,3-dihydrobenz[d]isothiazole-1,1-dioxide having the formula

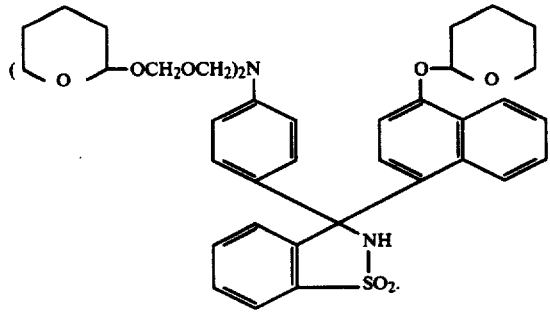

(b) The compound prepared in step (a) (0.03 g.) was dissolved in 10 ml. of anhydrous pyridine and 0.5 ml. of acetyl chloride was added. (A white precipitate formed.) The reaction solution was stirred for two hours, poured into water, extracted with chloroform and the chloroform extract dried over anhydrous sodium sulfate. The chloroform solution was evaporated to dryness, ethanol was added and the ethanol solution cooled. The precipitate that formed was collected to give the 2-acetyl derivative of the compound of step (a) as a white solid.

(c) The compound prepared in step (b) was placed in methanol with a drop of conc. HCl and the solution refluxed for two hours. The methanol was removed by evaporation, and the title compound was isolated via preparative TLC.

The 3-[4'-N,N-di($\beta$-2''-tetrahydropyranyloxyethyl)-1'-phenyl]benz[d]isothiazole-1,1-dioxide was prepared as follows:

4-Bromo-N,N-di($\beta$-2'-tetrahydropyranyloxyethyl)aniline (10.0 g.) was dissolved in 100 ml. of tetrahydrofuran. The solution was cooled to −65° C. and 10 ml. of n-butyllithium (2.4 M in hexane) was added dropwise under nitrogen at a rate to maintain the temperature below −65° C.

In a separate flask, saccharin (4.28 g.) was dissolved in 50 ml. of tetrahydrofuran under nitrogen, and the solution was cooled to −65° C. n-Butyllithium (2.4 M in hexane) was added until a peach color persisted (about 9.0 ml.)

The latter solution of the N-lithium salt of saccharin was added to the aniline solution by hollow wire over a 10 minute period. (Initially a green color formed which changed to tan.) The reaction mixture was stirred for 1.5 hours and poured into 2 liters of water. The pH was adjusted to 6 with conc. HCl, and the mixture extracted with ether. The ether extract was dried and evaporated and the residue was dissolved in 100 ml. of toluene. Two spatula tips of toluene sulfonic acid monohydrate were added, and the solution was refluxed for about 6 hours. The toluene was evaporated and the residue was dissolved in 2 liters of ether. The ether solution was cooled and the crystalline solid was collected to give 4.0 g. of the title compound (melting range 100°-101° C.).

EXAMPLES 5 AND 6

Preparation of the compounds having the formulae

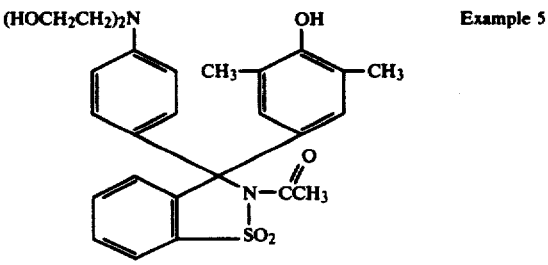

Example 5

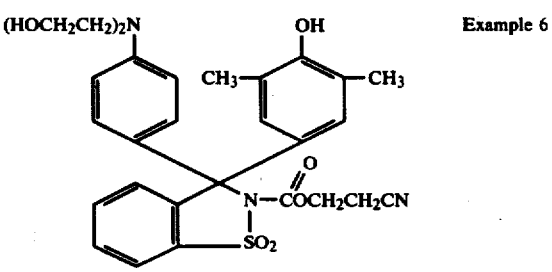

Example 6

The title compounds were prepared in the same manner as described in Example 4 and using in step (a), 4-bromo-2,6-dimethyl-methylene methoxyphenyl ether, and using in step (b), acetyl chloride and $\beta$-cyanoethylchloroformate, respectively.

EXAMPLE 7

Preparation of the compound having the formula

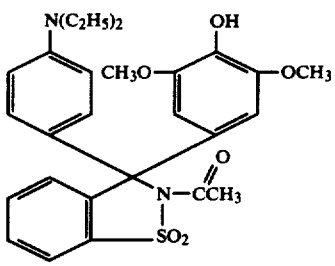

(a) 4-Bromo-2,6-dimethoxy-methylene methoxyphenyl ether (0.9 g.) was dissolved in 25 ml. of tetrahydrofuran under nitrogen. The solution was cooled to −65° C. and 1.4 ml. of n-butyllithium (2.4 M hexane) was added dropwise. After stirring for 45 minutes, 3-(4'-N,N-diethylamino-1'-phenyl)benz[d]isothiazole-1,1-dioxide (1.0 g.) was added, and the reaction mixture was allowed to warm to −40° C. The reaction mixture was cooled to −65° C., stirred for one hour, poured into water and the pH adjusted to 6 with conc HCl. The mixture was extracted with ether, the ether extract dried over anhydrous sodium sulfate and filtered. A solution of 0.22 g. sodium hydroxide in 5 ml. of water was added to the filtered ether solution and stirred several hours. The light yellow solid that formed was filtered, washed well with ether and then dissolved in about 200 ml. of water. The aqueous solution was neutralized with HCl to give a light yellow precipitate. The precipitate was filtered and vacuum dried to yield 0.9 g. of 3-(4'-N,N-diethylamino-1'-phenyl)-3-(2'',5''-dimethoxy-4''-methoxymethoxy-1''-phenyl)-2,3-dihydrobenz[d]isothiazole-1,1-dioxide.

(b) The compound prepared in step (a) (0.9 g.) was dissolved in 20 ml. of pyridine at room temperature, and acetyl chloride (2.0 ml.) was added. (A white precipitate formed.) The reaction mixture was stirred overnight, poured into water and extracted with chloroform. The chloroform extract was dried and the solvent removed by evaporation leaving a residue.

(c) The residue comprising the 2-acetyl derivative of the compound prepared in step (a) was dissolved in 50 ml. of methanol. Two drops of conc. HCl were added and the solution was refluxed for 4 hours. The solution was then evaporated under reduced pressure and the residue dissolved in isopropanol and cooled. The dark precipitate that formed was filtered and discarded. The isopropanol was evaporated, and the residue dissolved in a minimum of methylene chloride. Preparative TLC of a sample on silica gel with 9.7 ml. methylene chloride/0.3 ml. methanol gave 0.076 g. of the title compound.

The 3-(4'-N,N-diethylamino-1'-phenyl)benz[d]isothiazole-1,1-dioxide was prepared as follows:

4Bromo-N,N-diethylaniline (22.8 g.) was dissolved in 100 ml. of anhydrous tetrahydrofuran under nitrogen and then cooled to −74° C. To this solution was added dropwise 41.8 ml. of n-butyllithium (2.4 M in hexane) over a 50 minute period. (The temperature was maintained at −70° C. during the addition.) The solution was stirred for one hour. Then a solution of the N-lithium salt of saccharin in 100 ml. of tetrahydrofuran was added dropwise to the aniline solution at −70° C. using a double-ended needle. The resulting reaction mixture was stirred for 4 hours, poured slowly into 1 liter of water and the pH adjusted to 6 with conc. HCl. An orange precipitate formed which was filtered, dried and dissolved in 250 ml. of methanol containing about 5 ml. of conc. HCl. The solution was refluxed for 30 minutes and the precipitate collected to give 14.0 g. of the title compound (melting range 207°-208° C.).

Methoxymethylation of 4-bromo-2,6-dimethoxymethylene-methoxyphenyl ether was carried out using the same procedure given above for the methoxymethylation of 4-bromo-2,6-dimethyl-methylenemethoxyphenyl ether.

EXAMPLES 8-10

Preparation of the compounds having the formulae

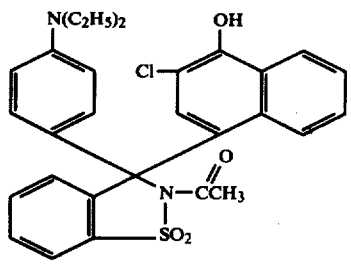

Example 8

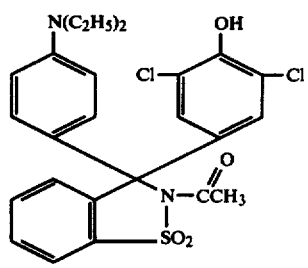

Example 9

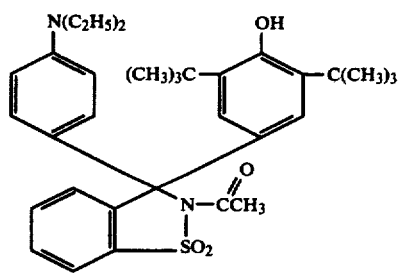

Example 10

The title compounds were prepared according to the procedure given in Example 7 above except that the blocked 1-naphthol and phenols were the 2'-tetrahydropyranyl ether of 4-bromo-2-chloro-1-naphthol, the 2'-tetrahydropyranyl ether of 4-bromo-2,6-dichlorophenol and the trimethylsilyl ether of 4-bromo-2,6-tert. butylphenol, respectively.

The preparation of the trimethylsilyl ether of 4-bromo-2,6-di-tert. butylphenol was carried out as follows:

4-Bromo-2,6-di-tert-butylphenol (7.0 g.; 0.024 mol.) was dissolved in 25 ml. of dry tetrahydrofuran under nitrogen and cooled to −10° C. to −5° C. n-Butyllithium (2.7 M in hexane; 8.8 ml.; 0.024 mol.) was added dropwise. (A precipitate formed.) The mixture was stirred for 15 minutes at 5° C. and trimethylsilylchloride (3.0 ml.; 0.03 mol.) was added which was just enough to give a positive acid test for a hydrolyzed sample. The reaction mixture was then refluxed for one hour, cooled and 20 ml. of water was added and stirred. A pale yellow solid formed. The solid was collected, dissolved in hot benzene and diluted with hot methanol. On cooling white crystals formed and were collected to give 6.27 g. of the title compound (melting range 144°–145.5° C.).

The 2'-tetrahydropyranyl ethers of 4-bromo-2-chloro-1-naphthol and 4-bromo-2,6-dichlorophenol were prepared in the same manner as described above for the preparation of the 2'-tetrahydropyranyl ether of 4-bromo-1-naphthol.

EXAMPLE 11

Preparation of the compound having the formula

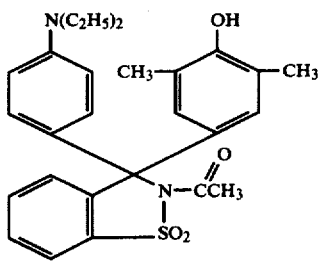

(a) To approximately 125 ml. of dry tetrahydrofuran under a nitrogen blanket was added 4-bromo-2,6-dimethylmethylenemethoxyphenyl ether (1.2 g.) and the solution cooled to −75° C. with stirring. 4.18 ml. of n-butyllithium (2.4 M in hexane) in 10 ml. of dry tetrahydrofuran was added dropwise to the phenyl ether solution over 15 minutes and the mixture stirred cold for 30 minutes. 1.5 g. of 3-(4'-N,N-diethylamino-1'-phenyl)benz[d]isothiazole-1,1-dioxide was added and the cold reaction mixture stirred vigorously. The reaction mixture was allowed to come to room temperature overnight, cooled in an ice water bath and treated with excess aqueous ammonium chloride solution. The organic portion was decanted, dried over anhydrous calcium sulfate and the solvent removed under reduced pressure leaving a yellow oil. The oil was extracted with several portions of petroleum ether to give a light yellow solid. Recrystallization from 45 mls. of 1-propanol gave an off-white solid that was washed with 1-propanol and dried under vacuum to give 1.1 g. of 3-(4'-N,N-diethylamino-1'-phenyl)-3-(4''-methoxymethoxy-3'',5''-dimethyl-1''-phenyl)-2,3-dihydrobenz[d]isothiazole-1,1-dioxide.

(b) The compound prepared in step (a) (0.120 g.) was added to 25 ml. of dry dioxane under a nitrogen blanket at room temperature. Then 0.120 g. of sodium hydride (50% oil dispersion) was added. After stirring at room temperature for 45 minutes, a solution of acetyl chloride (0.390 g.) dissolved in a small amount of dioxane was added. The reaction mixture was stirred at room temperature for 45 minutes and poured into 125 mls. of ice water saturated with sodium chloride. The mixture was extracted with chloroform, the chloroform extract dried over anhydrous calcium sulfate and the solvent removed. The residue was extracted with petroleum ether and dried under vacuum to give the N-acetyl derivative of the compound prepared in step (a) as an off-white solid.

(c) The compound prepared in step (b) was dissolved in 20 mls. of methanol and 2 drops of conc. HCl was added. The solution was heated on a steam bath for 40 minutes, the solvent removed under reduced pressure and the residue extracted with petroleum ether. The ether extract was dried under vacuum to give a pink solid. The title compound was obtained by preparative TLC using 60:40 ethylacetate/petroleum ether.

The 3-(carbocyclic aryl)-benz[d]isothiazole-1,1-dioxides having the formulae

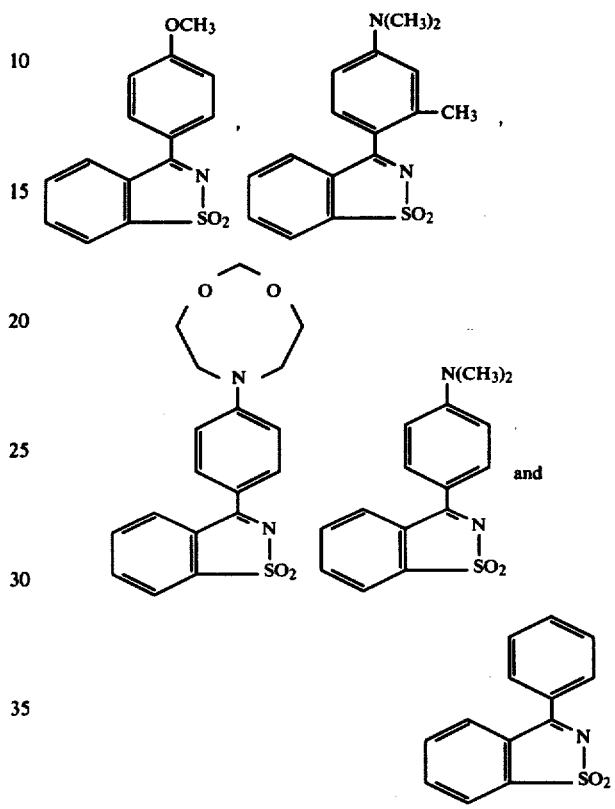

and were prepared according to the same procedure given above for the preparation of 3-(4'-N-morpholinyl-1'-phenyl)benz[d]isothiazole-1,1-dioxide by converting the selected 4-halo starting compounds to the 4-lithium derivatives and reacting them with the N-lithium derivative of saccharin.

The N-(4-halophenyl)tetrahydro-2H,4H-1,3,6-dioxazocines are prepared by reacting a 4-halo-N,N-di(β-hydroxyethyl)aniline with certain dihalomethanes in the presence of a solid alkali metal hydroxide or concentrated aqueous solution thereof and a quaternary ammonium salt. These compounds and their preparation form the subject matter of U.S. patent application Ser. No. 836,066 of Louis Cincotta, James W. Foley and Marcis M. Kampe filed concurrently herewith.

3-(4'-N,N-dimethylamino-1'-phenyl)benz[d]isothiazole-1,1-dioxide was prepared as follows:

To 20 ml. of tetrahydrofuran under a nitrogen blanket was added 2.4 g. of magnesium turnings. Then a solution of 20.0 g. of 4-bromo-N,N-dimethylaniline in 80 ml. of tetrahydrofuran was added gradually over one hour and the mixture heated for an additional 30 minutes and allowed to cool to room temperature. Separately, a solution of 9.0 g. of saccharin in 200–250 ml. of tetrahydrofuran was cooled to −78° C. The Grignard mixture was slowly added with stirring under nitrogen to the cold saccharin solution at a rate to maintain the temperature at about −78° C. The reaction mixture was allowed to come to room temperature overnight and then cooled in an ice water bath. Saturated cold ammonium chloride solution was added, the yellow-green organic portion was decanted and the aqueous portion was extracted with more tetrahydrofuran. The combined tetrahydrofuran extracts were washed with water and dried over anhydrous magnesium sulfate. The tetrahydrofuran was removed under reduced pressure and the residue extracted with petroleum ether to give 8.7 g. of the title compound as a green-yellow solid.

Tetrahydropyranylation of p-Br-N,N-di($\beta$-hydroxyethyl)aniline was carried out as follows:

p-Br-N,N-di($\beta$-hydroxyethyl)aniline (20.0 g.) was dissolved in 475 ml. of dichloromethane containing 60 ml. of dihydropyran. To this solution was added 1 ml. of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g. of the title compound.

The methoxymethyl ethers of 4-bromophenol and of 4-bromo-1-naphthol were prepared according to the procedures described above. The 2'-tetrahydropyranyl ethers of 4-bromo-2,6-diisopropyl-phenol and of 4-bromo-2,6-dimethylphenol also were prepared according to the procedures described above.

The dimethyl-t-butylsilyl ether of 4-bromo-1-naphthol was prepared as follows:

4-Bromo-1-naphthol (22.1 g.) and dimethyl-t-butylsilyl chloride (18.1 g.) were dissolved in 50 ml. of dimethylformamide at room temperature. The resulting solution was cooled in an ice bath and imidazole (17.0 g.) added under nitrogen. (A slight exotherm was observed.) A solid precipitated and the reaction mixture was stirred overnight.

The reaction mixture was poured into 1500 ml. of water at about 20° C. with stirring. The pH was adjusted to 4-5 with dilute HCl, and the solids were filtered, washed with water, and air dried for 2 hours and dissolved in 150 ml. of boiling isopropanol. The isopropanol solution was filtered while hot and then cooled slowly to room temperature. Crystals began to form and after standing at room temperature overnight, the solution was cooled in an ice water bath for 1 hour and filtered. The solid collected was washed with small amounts of isopropanol, air dried briefly and then dried in vacuo for 2 hours to give 24.3 g. of the title compound (melting range 70°–73° C.).

It will be appreciated that the halo derivatives of these blocked phenols and 1-naphthol may be converted to the corresponding lithium reagent for reaction with the selected 3-(phenyl/naphthol)benz[d]isothiazole-1,1-dioxide to give the corresponding 3-(phenyl/naphthyl)-3-(4'-OP-1'-phenyl/4'-OP-1'-naphthyl)-2,3-dihydrobenz[b]isothiazole-1,1-dioxide.

Where it is desired to prepare sulfamnaphthaleins, 2,3-dihydro-3-oxo-naphtho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with PCl₅ in the same manner as the preparation of saccharin pseudo-chloride.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl/naphthyl or 4'-substituted phenyl/4'-substituted naphthyl moiety as the other of the 3,3 substituents form the subject matter of copending U.S. patent application Ser. No. 836,021 of Stanley M. Bloom, Alan L. Borror and James W. Foley filed concurrently herewith and of copending U.S. patent applications Ser. Nos. 835,998; 836,005; and 836,009 of Stanley M. Bloom, Alan L. Borror and James W. Foley also filed concurrently herewith. As discussed in the aforementioned applications, compounds may be selected for use as classical pH-sensitive dyes or as photographic optical filter agents and filter agent precursors depending upon the 2-substituent of the benz[d]isothiazole ring. The photographic use of certain of the compounds as photographic optical filter agents and filter agent precursors forms the subject matter of copending U.S. patent application Ser. No. 836,006 of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S. patent application Ser. No. 836,067 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

Since certain changes may be made in the above processes without departing from the scope of the invention herein involved, it is intended that all matter contained in the above description shall be interpreted as illustrative and not in a limiting sense.

What is claimed is:

1. A process which comprises
   (1) reacting (a) a 4-OP-carbocyclic aryllithium compound wherein P is a protecting group selected from a 4-OP-phenyllithium compound and a 4-OP-naphthyllithium compound and (b) a compound of the formula

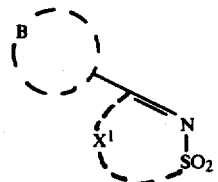

wherein B is a carbocyclic aryl moiety other than a 4'-OP-carbocyclic aryl moiety selected from a phenyl moiety and a naphthyl moiety and $X^1$ represents the atoms necessary to complete a benz[d]isothiazole-1,1-dioxide moiety or a naphtho[1,8-de]-1,2-thiazine-1,1-dioxide moiety in an inert solvent at a temperature between about −80° and 50° C. to give (c) the compound having the formula

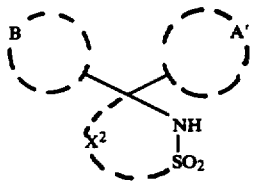

wherein A' is a 4'-OP-1'-phenyl moiety or a 4'-OP-1'-naphthyl moiety; P is a protecting group; B has the same meaning given above; and $X^2$ represents the atoms necessary to complete a 2,3-dihydrobenz[d]isothiazole-1,1-dioxide moiety or a 2,3-dihydronaphtho[1,8-de]-1,2-thiazine-1,1-dioxide moiety;

(2) reacting said compound (c) with an excess of an acid halide of the formula W-Z wherein W is chloro or bromo and Z is a carbonyl moiety containing a

group in pyridine at a temperature between about 0° C. and 100° C. to yield (d) the corresponding acylated compound having the formula

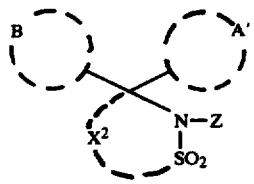

wherein A', B and $X^2$ have the same meaning given above and Z is said carbonyl moiety and said

is bonded to said N atom; and (3) treating said compound (d) with an organic or inorganic acid at a pH between about 0.1 and 5.0 at a temperature between about 20° and 100° C. to give (e) the compound having the formula

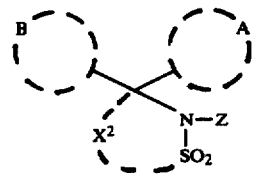

wherein A is a 4'-OH-1'-phenyl moiety or a 4'-OH-1'-naphthyl moiety and B, $X^2$ and Z have the same meaning given above.

2. A process as defined in claim 1 wherein said (a) is a 4-OP-phenyllithium compound.

3. A process as defined in claim 1 wherein said (a) is a 4-OP-naphthyllithium compound.

4. A process as defined in claim 1 wherein said $X^1$ represents the atoms necessary to complete a benz[d]isothiazole-1,1-dioxide moiety.

5. A process as defined in claim 1 wherein said B is a phenyl moiety.

6. A process as defined in claim 1 wherein said B is a naphthyl moiety.

7. A process which comprises (1) reacting (a) a compound of the formula

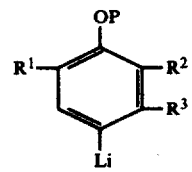

wherein P is a protecting group; $R^1$ and $R^2$ each are selected from hydrogen, alkyl, alkoxy, chloro and fluoro; $R^3$ is hydrogen, alkyl, alkoxy or —OP; and $R^2$ and $R^3$ taken together represent the carbon atoms necessary to complete a fused benzene ring and (b) a compound having the formula

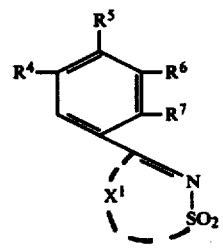

wherein $R^4$ and $R^6$ each are selected from hydrogen, alkyl, alkoxy, chloro and fluoro; $R^5$ is hydrogen, alkyl, alkoxy, —N,N-(dialkyl)amino, —N,N-(w-$R^8$alkyl)$_2$amino wherein $R^8$ is halo or —OP$^I$ wherein P$^I$ is a protecting group, —NHCOCH$_3$, piperidino, pyrrolidino, N-methylpiperazino, morpholino, thiomorpholino or tetrahydro-2H,4H-1,3,6-dioxazocino; $R^7$ is hydrogen, alkyl, alkoxy or —OP$^{II}$ wherein P$^{II}$ is a protecting group the same as P$^I$; $R^6$ and $R^7$ taken together represent the carbon atoms necessary to complete a fused benzene ring; $R^4$, $R^5$ and $R^6$ taken together represent the atoms necessary to complete a fused [ij]quinolizidine ring and $X^1$ represents the atoms necessary to complete benz[d]isothiazole-1,1-dioxide or naphtho[1,8-de]-1,2-thiazine-1,1-dioxide in an inert organic solvent at a temperature between about −80° C. and 50° C. to give (c) the compound having the formula

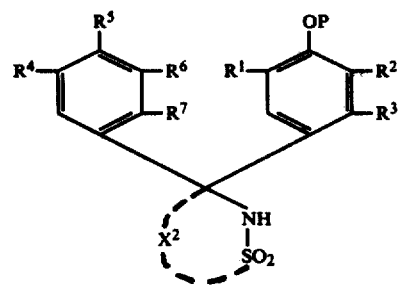

wherein P, $R^1$, $R^2$, $R^3$, $R^4$, $R^5$, $R^6$ and $R^7$ have the same meaning given above and $X^2$ represents the atoms necessary to complete 2,3-dihydrobenz[d]isothiazole-1,1-dioxide or 2,3-dihydronaphtho[1,8-de]-1,2-thiazine-1,1-dioxide;

(2) reacting said compound (c) with an excess of an acid halide of the formula W-Z wherein W is chloro or bromo and Z is a carbonyl moiety containing a

group in pyridine at a temperature between about 0° and 100° to yield (d) the corresponding N-acylated compound of the formula

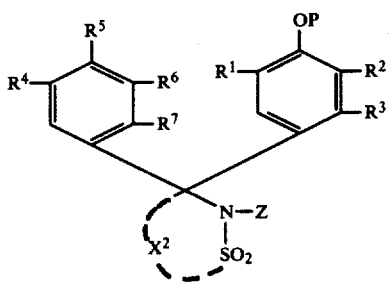

wherein P, $R^1$, $R^2$, $R^3$, $R^4$, $R^5$, $R^6$, $R^7$ and $X^2$ have the same meaning given above and Z is said carbonyl moiety and said

is bonded to said N atom; and (3) treating said compound (d) at a temperature between about 20° and 100° C. with an organic or inorganic acid at a pH between about 0.1 and 5.0 to yield the product having the formula

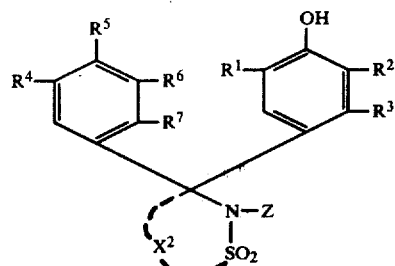

wherein $R^1$, $R^2$, $R^3$, $R^4$, $R^5$, $R^6$, $R^7$, Z and $X^2$ have the same meaning given above except that said —OP of $R^3$, said —$OP^I$ of $R^5$, and said —$OP^{II}$ of $R^7$ each are —OH.

8. A process as defined in claim 7 wherein $X^2$ represents the carbon atoms necessary to complete benz[d]isothiazole-1,1-dioxide.

9. A process as defined in claim 7 wherein $R^7$ is hydrogen.

10. A process as defined in claim 9 wherein $R^4$, $R^5$ and $R^6$ taken together represent the atoms necessary to complete a fused [ij]quinolizidine ring.

11. A process as defined in claim 7 wherein $R^4$ and $R^6$ each are hydrogen and $R^5$ and $R^7$ each are alkyl.

12. A process as defined in claim 7 wherein $R^4$, $R^5$, $R^6$ and $R^7$ each are hydrogen.

13. A process as defined in claim 7 wherein $R^4$, $R^6$ and $R^7$ each are hydrogen.

14. A process as defined in claim 13 wherein $R^5$ is alkyl.

15. A process as defined in claim 13 wherein $R^5$ is —N,N-dialkyl(amino).

16. A process as defined in claim 13 wherein $R^5$ is morpholino.

17. A process as defined in claim 13 wherein $R^5$ is alkoxy.

18. A process as defined in claim 13 wherein $R^5$ is tetrahydro-2H,4H-1,3,6-dioxazocino.

19. A process as defined in claim 13 wherein $R^5$ is —N,N-(w-$R^8$alkyl)$_2$amino wherein $R^8$ is —$OP^I$.

20. A process as defined in claim 7 wherein $R^3$ is hydrogen.

21. A process as defined in claim 20 wherein $R^1$ and $R^2$ are alkyl.

22. A process as defined in claim 20 wherein $R^1$ and $R^2$ are alkoxy.

23. A process as defined in claim 20 wherein $R^1$ and $R^2$ are chloro.

24. A process as defined in claim 7 wherein $R^2$ and $R^3$ taken together represent the carbon atoms necessary to complete a fused benzene ring.

25. A process as defined in claim 24 wherein $R^1$ is hydrogen.

26. A process as defined in claim 24 wherein $R^1$ is chloro.

* * * * *